United States Patent [19]

Ueda et al.

[11] Patent Number: 4,675,324
[45] Date of Patent: Jun. 23, 1987

[54] SUBSTITUTED PYRAZOLO [4,3-C]PYRIDINES AND THEIR USE AS URICOSURIC, DIURETIC AND ANTI-HYPERTENSIVE AGENTS

[75] Inventors: Ikuo Ueda, Uenohigashi; Youichi Shiokawa, Ibaraki; Takashi Manabe, Kawanishi; Yousuke Katsura, Uenonishi, all of Japan

[73] Assignee: Fujisawa Pharmaceutical Co., Ltd., Osaka, Japan

[21] Appl. No.: 780,582

[22] Filed: Sep. 26, 1985

[30] Foreign Application Priority Data

Oct. 26, 1984 [GB] United Kingdom ................. 8427124
May 28, 1985 [GB] United Kingdom ................. 8513399

[51] Int. Cl.$^4$ .................. A61K 31/395; C07D 471/04
[52] U.S. Cl. ..................................... 514/293; 546/82
[58] Field of Search ........................... 546/82; 514/293

[56] References Cited

U.S. PATENT DOCUMENTS 3,679,699 7/1972 Oppolzer ........................... 546/82
4,524,146 6/1985 Yokuyama ......................... 546/82

OTHER PUBLICATIONS

M. T. DiParsia, et al., J. Med. Chem, (1981) 24, 117–119.
W. N. Speckamp, et al., Rec. Trav. Chim, (1966) 85, 681–693.

Primary Examiner—Henry R. Jiles
Assistant Examiner—J. Richter
Attorney, Agent, or Firm—Oblon, Fisher, Spivak, McClelland & Maier

[57] ABSTRACT

This invention provides a benezene-fused heterocyclic compound of the formula:

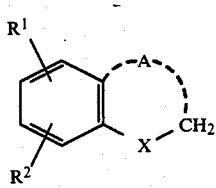

wherein
R$^1$ is halogen, nitro, amino, hydroxy, lower alkyl, lower alkoxy substituted by carboxy or protected carboxy, acylamino which may have lower alkyl on the amino moiety, or aryloxy which may have halogen,
R$^2$ is hydrogen or halogen,
X is —O— or

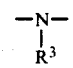

in which R$^3$ is hydrogen, lower alkyl or acyl and A is a group of the formula:

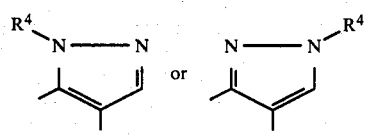

in which
R$^4$ is hydrogen, lower alkenyl, lower alkynyl or alkyl which may have suitable substituent(s) selected from the groups consisting of hydroxy, acyl, lower alkoxy, di(lower)alkylamino, carboxy, protected carboxy and aryl; or
R$^1$ is hydrogen or lower alkoxy,
R$^2$ is hydrogen,
X is

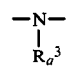

in which R$_a^3$ is lower alkanoyl and
A is a group of the formula:

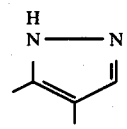

and pharmaceutically acceptable salts thereof. This compound possesses diuretic activity, uricosuric activity and vasodilative activity and are useful as a diuretic agent, uricosuric agent and anti-hypertensive agent. The invention further relates to processes for the preparation of this compound and pharmaceutical composition comprising compound of the above formula.

19 Claims, No Drawings

SUBSTITUTED PYRAZOLO [4,3-c]PYRIDINES AND THEIR USE AS URICOSURIC, DIURETIC AND ANTI-HYPERTENSIVE AGENTS

This invention relates to a new benzene-fused heterocyclic compound and pharmaceutically acceptable salt thereof.

More particularly, it relates to a new benzene-fused heterocyclic compound and pharmaceutically acceptable salt thereof which have diuretic activity, uricosuric activity and vasodilative activity, to processes for preparing thereof and to a pharmaceutical composition comprising the same.

The objective benzene-fused heterocyclic compound can be represented by the following formula:

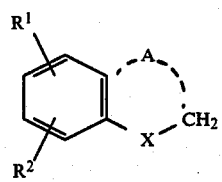

wherein
$R^1$ is halogen, nitro, amino, hydroxy, lower alkyl, lower alkoxy substituted by carboxy or protected carboxy, acylamino which may have lower alkyl on the amino moiety, or aryloxy which may have halogen,
$R^2$ is hydrogen or halogen,
X is —O— or

in which $R^3$ is hydrogen, lower alkyl or acyl and
A is a group of the formula:

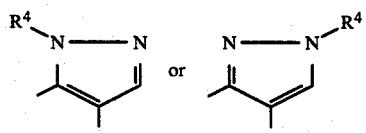

in which
$R^4$ is hydrogen, lower alkenyl, lower alkynyl or alkyl which may have suitable substituent(s) selected from the groups consisting of hydroxy, acyl, lower alkoxy, di(lower)alkylamino, carboxy, protected carboxy and aryl; or
$R^1$ is hydrogen or lower alkoxy,
$R^2$ is hydrogen,
X is

in which $R_a^3$ is lower alkanoyl and
A is a group of the formula:

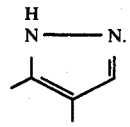

The object compound (I) of this invention includes tautomeric isomers. That is, in case that the symbol "$R^4$" in the object compound (I) is hydrogen, said object compound (I) can be represented by the following tautomeric equilibrium.

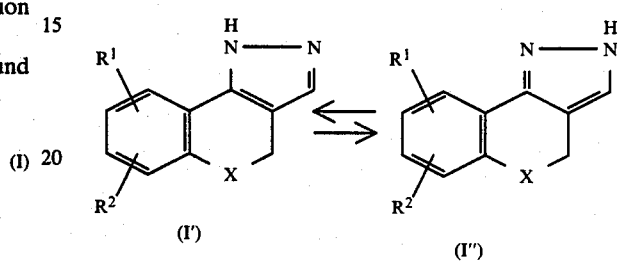

This type of tautomerism as stated above is well known, and it is obvious to any person skilled in the arts that the both tautomeric isomers are easily convertible reciprocally and are included within the category of the same compound.

Accordingly, the both tautomeric isomers are clearly included within the scope of the object compound (I) of this invention. In the present specification and claims, said object compound (I) including both tautomeric isomers is represented by using the one of expressions, namely, the formula (I') only for the convenience' sake.

Suitable pharmaceutically acceptable salts of the object compound (I) are conventional non-toxic salts and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

According to this invention, the new benzene-fused heterocyclic compound (I) and pharmaceutically acceptable salt thereof can be prepared by, for example, the following processes.

Process 1:

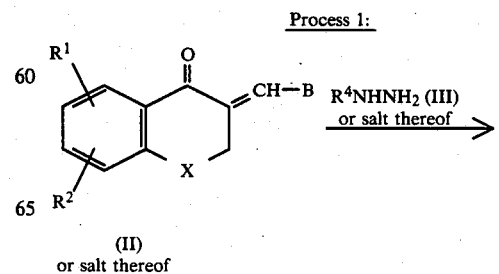

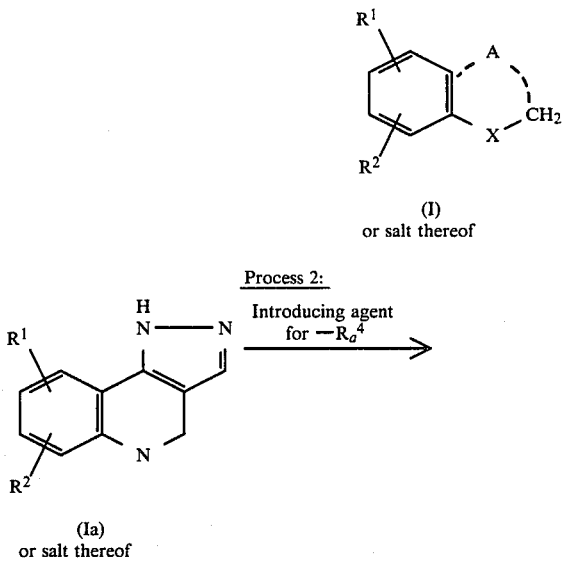

(I)
or salt thereof

Process 2:

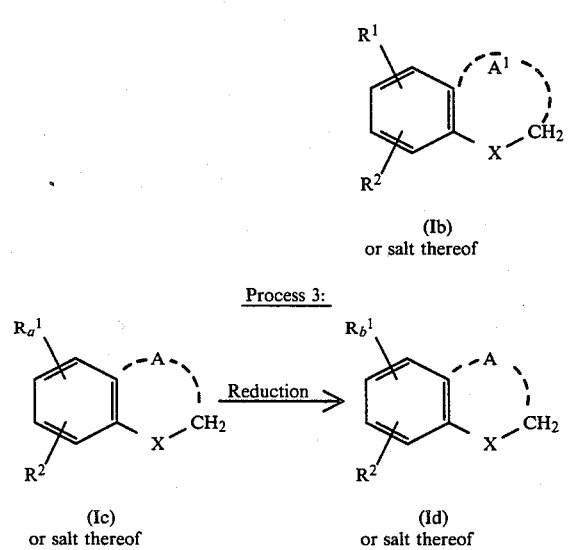

(Ia)
or salt thereof

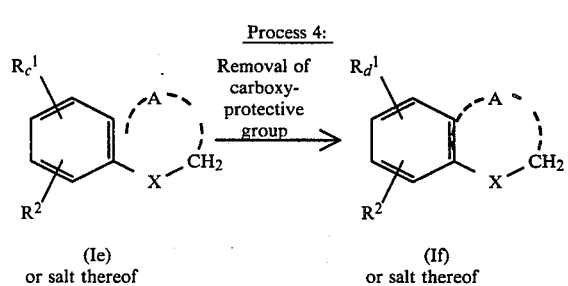

(Ib)
or salt thereof

Process 3:

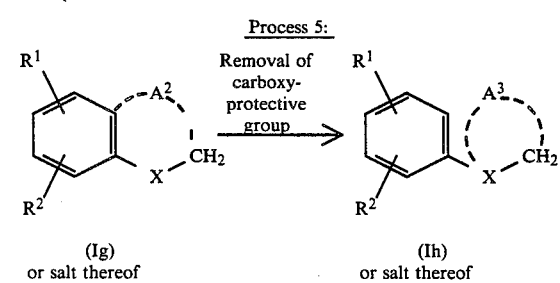

(Ic)                (Id)
or salt thereof    or salt thereof

Process 4:
Removal of carboxy-protective group

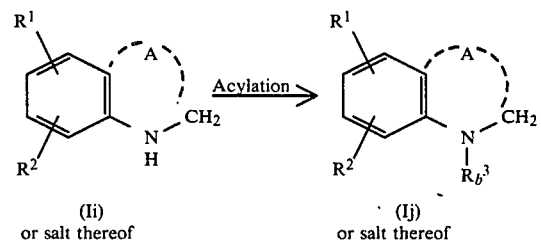

(Ie)               (If)
or salt thereof   or salt thereof

Process 5:
Removal of carboxy-protective group (Ig)               (Ih)
or salt thereof   or salt thereof Process 6:

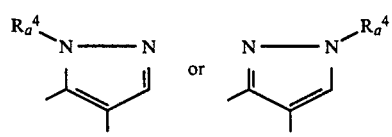

(Ii)               (Ij)
or salt thereof   or salt thereof wherein
R$^1$, R$^2$, A and X are each as defined above, and
R$_a^1$ is nitro,
R$_b^1$ is amino,
R$_c^1$ is lower alkoxy substituted by protected carboxy,
R$_d^1$ is lower alkoxy substituted by carboxy,
R$_b^3$ is acyl,
A$^1$ is a group of the formula:

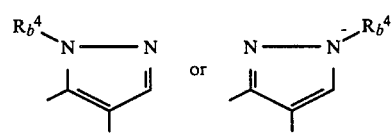

in which
R$_a^4$ is lower alkenyl, lower alkynyl or alkyl which may have suitable substituent(s) selected from the groups consisting of hydroxy, acyl, lower alkoxy, di(lower)alkylamino, carboxy, protected carboxy and aryl,
A$^2$ is a group of the formula:

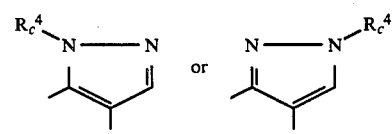

in which
R$_b^4$ is alkyl substituted by protected carboxy,
A$^3$ is a group of the formula:

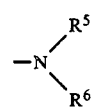

in which R$_c^4$ is alkyl substituted by carboxy, and B is hydroxy or a group of the formula $$-N\begin{array}{c}R^5\\R^6\end{array}$$

wherein R$^5$ and R$^6$ are each lower alkyl.

The starting compound (II) or salt thereof is a new compound and can be prepared by, for example, the following preparation and in a similar manner thereto.

Preparation

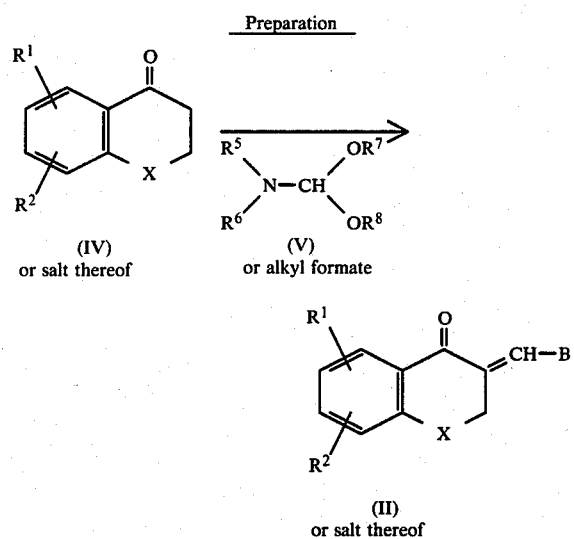

wherein $R^1$, $R^2$, $R^5$, $R^6$, B and X are each as defined above, and $R^7$ and $R^8$ are each lower alkyl.

The salts of compounds (Ia), (Ib), (Ic), (Id), (Ie), (If), (Ih), (Ii), (Ij), (II) and (IV) are the same as those exemplified for the pharmaceutically acceptable salt of the object compound (I) mentioned above.

The salt of compound (III) is an acid addition salt such as those exemplified for the pharmaceutically acceptable salt of the object compound (I) mentioned above.

In the above and subsequent descriptions of this specification, suitable examples and illustrations of the various definitions are explained in detail in the followings.

The term "lower" is intended to mean 1 to 6 carbon atom(s), unless otherwise indicated.

The term "higher" is intended to mean more than 6 carbon atoms, preferably 7 to 22 carbon atoms and more preferably 7 to 18 carbon atoms.

"Halogen" may include fluorine, chlorine, bromine and iodine.

Suitable "alkyl" may include "lower alkyl" (e.g. methyl, ethyl, propyl, isopropyl, butyl, isobutyl, t-butyl, pentyl, hexyl, etc.) and "higher alkyl" (e.g. heptyl, octyl, tetradecyl, etc.).

Suitable "lower alkoxy" may include methoxy, ethoxy, propoxy, isopropoxy, butoxy, isobutoxy, t-butoxy, pentyloxy, hexyloxy and the like.

Suitable "protected carboxy" may include esterified carboxy such as lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl) and the like.

The "acyl" and "acyl" moiety in the term "acylamino" may include the residue of organic acid such as organic carboxylic acid, organic sulfonic acid, organic carbamic acid, organic carbonic acid and the like.

The "acylamino" includes both of monoacylamino and diacylamino.

Suitable "acyl" may be alkanoyl such as lower alkanoyl (e.g. formyl, acetyl, propionyl, butyryl, isobutyryl, 3,3-dimethylbutyryl, valeryl, isovaleryl, pivaloyl) which may have suitable substituent(s) such as lower alkoxy (e.g. methoxy, ethoxy, propoxy, etc.) or higher alkanoyl (e.g. heptanoyl, 2,3-dimethylpentanoyl, lauroyl, myristoyl, palmitoyl, stearoyl), lower cycloalkylcarbonyl having 4 to 8 carbon atoms (e.g. cyclopropylcarbonyl, cyclobutylcarbonyl, cyclopentylcarbonyl, cyclohexylcarbonyl, cycloheptylcarbonyl), lower alkoxycarbonyl (e.g. methoxycarbonyl, ethoxycarbonyl, propoxycarbonyl), lower alkanesulfonyl (e.g. mesyl, ethanesulfonyl, propanesulfonyl), lower alkylcarbamoyl (e.g. methylcarbamoyl, ethylcarbamoyl, propylcarbamoyl) and the like.

Suitable "aryloxy" may include phenoxy, tolyloxy, naphthyloxy and the like.

Suitable "di(lower)alkylamino" may include dimethylamino, diethylamino, dipropylamino and the like.

Suitable "lower alkenyl" having 2 to 6 carbon atoms may include vinyl, allyl, butenyl, pentenyl, hexenyl and the like.

Suitable "lower alkynyl" having 2 to 6 carbon atom may include ethynyl, 2-propynyl, 2-butynyl 2-hexynyl and the like.

Suitable "aryl" may include phenyl, tolyl, xylyl, naphthyl and the like.

Preferable embodiments of the object compound (I) are as follows.

Preferable embodiment of $R^1$ is halogen, nitro, amino, hydroxy, lower alkyl, carboxy(lower)alkoxy, protected carboxy(lower)alkoxy[more preferably esterified carboxy(lower)alkoxy[most preferably lower alkoxycarbonyl(lower)alkoxy]], acylamino[more preferably lower alkanoylamino], N-lower alkyl-N-acylamino[more preferably N-lower alkyl-N-lower alkanesulfonylamino]or haloaryloxy[more preferably halophenoxy]; $R^2$ is hydrogen or halogen; X is —O— or

in which $R^3$ is hydrogen, lower alkyl or acyl[more preferably lower alkanoyl which may have lower alkoxy, higher alkanoyl, lower cycloalkylcarbonyl, lower alkoxycarbonyl, lower alkanesulfonyl or lower alkylcarbamoyl]; and $R^4$ is hydrogen, lower alkenyl, lower alkynyl, lower or higher alkyl, hydroxy(lower)alkyl, acyl(lower)alkyl[more preferably lower alkanoyl(lower)alkyl], lower alkoxy(lower)alkyl, di(lower)alkylamino(lower)alkyl, carboxy(lower)alkyl, protected carboxy(lower)alkyl[more preferably esterified carboxy(lower)alkyl [most preferably lower alkoxycarbonyl(lower)alkyl]] or ar(lower)alkyl[more preferably phenyl(lower)alkyl] or $R^1$ is hydrogen or lower alkoxy; $R^2$ is hydrogen; X is

in which $R_a^3$ is lower alkanoyl; and $R^4$ is hydrogen.

The processes and preparation as illustrated above are explained in more detail in the followings.

Process 1

The object compound (I) or salt thereof can be prepared by reacting the compound (II) or salt thereof with the compound (III) or salt thereof.

This reaction is usually carried out in a solvent which does not adversely influence the reaction such as methanol, ethanol, propanol, tetrahydrofuran, chloroform, acetic acid and the like.

The reaction temperature is not critical and the reaction can be carried out under heating to under cooling.

When there is used the starting compound (II) having hydroxy for $R^1$, the hydroxy group may often protected by a conventional hydroxy-protective group such as acyl (e.g. lower alkanoyl, etc.) and the like. This case is included within the scope of this process.

Process 2

The compound (Ib) or salt thereof can be prepared by reacting the compound (Ia) or salt thereof with an introducing agent for $-R_a^4$.

The preferred introducing agent for $-R_a^4$ is a compound of the formula: $R_a^4Y$ wherein $R_a^4$ is the same as defined above and Y is an acid residue such as halogen.

This reaction is usually carried out in a solvent which does not adversely influence the reaction such as N,N-dimethylformamide, dimethylsulfoxide, tetrahydrofuran and the like.

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

The reaction temperature is not critical and the reaction can be carried out under cooling to under heating.

Process 3

The compound (Id) or salt thereof can be prepared by reducing the compound (Ic) or salt thereof.

The reduction is carried out in a conventional manner such as catalytic reduction, reduction with a reducing agent (e.g. iron and hydrochloric acid) and the like.

The catalyst of the catalytic reduction may include a conventional catalyst such as Raney nickel, palladium on carbon and the like.

The reaction is usually carried out in a solvent which does not adversely influence the reaction such as methanol, ethanol, propanol, ethyl acetate, tetrahydrofuran, dioxane and the like.

The reaction temperature is not critical and the reaction can be carried out under cooling to under heating and is sufficiently carried out at ambient temperature under atmospheric pressure.

Process 4

The compound (If) or salt thereof can be prepared by subjecting the compound (Ie) or salt thereof to removal reaction of carboxy-protective group.

The removal reaction of this process may include hydrolysis, reduction and the like.

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The reaction of this process is usually carried out in a solvent which does not adversely influence the reaction such as water, methanol, ethanol, propanol, acetic acid and the like, at a temperature range of cooling to heating.

Process 5

The compound (Ih) or salt thereof can be prepared by subjecting the compound (Ig) or salt thereof to removal reaction of carboxy-protective group.

The removal reaction is carried out in substantially the same manner as that of process 4.

Process 6

The compound (Ij) or salt thereof can be prepared by reacting the compound (Ii) or salt thereof with an acylating agent.

The acylating agent to be used in this reaction includes an organic acid (i.e. $R_b^3$ OH (IV), in which $R_b^3$ is acyl) and its reactive derivative.

The suitable reactive derivative of the compound (IV) may be a conventional one such as an acid halide (e.g. acid chloride, acid bromide, etc.), an acid azide, an acid anhydride, an activated amide, an activated ester, an isocyanate and the like.

When free acid is used as an acylating agent, the acylation reaction may preferably be conducted in the presence of a conventional condensing agent.

The reaction can preferably be conducted in the presence of an organic or inorganic base as those exemplified in the explanation of the above Process 2.

This reaction is usually carried out in a solvent which does not adversely influence the reaction such as methanol, ethanol, propanol, tetrahydrofuran, chloroform and the like.

The reaction temperature is not critical and the reaction can be carried out under heating to under cooling.

Preparation

The compound (II) or salt thereof can be prepared by reacting the compound (IV) or salt thereof with the compound (V) or alkyl formate.

The compound (IV) includes known compounds and novel ones. The known compounds, e.g. 6-chloro-4-oxo-1,2,3,4-tetrahydroquinoline can be prepared by the method described in Japanese Patent Early Publication Laid Open No. 28052/1982 and the other compounds can also be prepared in a similar manner thereto.

This reaction is usually conducted without or in a solvent which does not adversely influence the reaction such as benzene, toluene, xylene, chloroform and the like.

This reaction can preferably be carried out in the presence of an inorganic or organic base such as those exemplified in the explanation of process 2 mentioned above.

The reaction temperature is not critical and the reaction is preferably carried out under heating.

The object compound of the above processes 1–6 and preparation can be purified and converted to the desired salts in a conventional manner.

The object compound (I) of this invention and pharmaceutically acceptable salt thereof possess diuretic activity, uricosuric activity and vasodilative activity. Accordingly, the object compound (I) is useful for a diuretic agent, uricosuric agent and anti-hypertensive agent.

For illustration purpose, some pharmacological data of the object compound (I) are shown in the followings.

Test (Excretion of urine, electrolytes and uric acid in rats)

(1) Test compound
(a) a compound of the formula:

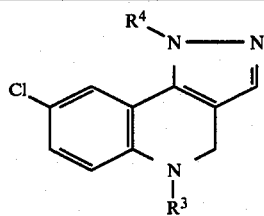

| Test compound No. | $R^3$ | $R^4$ |
|---|---|---|
| 1 | $-COC_2H_5$ | $-H$ |
| 2 | $-COC_2H_5$ | $-CH_3$ |
| 3 | $-H$ | $-CH_3$ |
| 4 | $-COC_2H_5$ | $-CH(CH_3)_2$ |

(b) a compound of the formula:

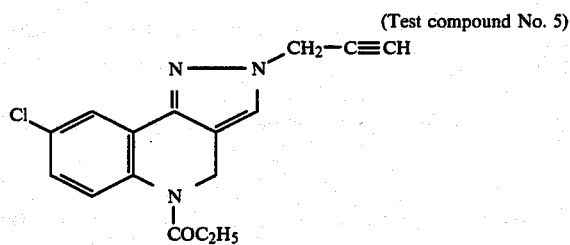

(Test compound No. 5)

(c) Test method:

Male Jcl:SD strain rats aged-6 weeks were used after being deprived of food starving for 18 hours. The test compound was orally given to test rats (dosage : 320 mg/kg). Immediately after dosing 20 ml/kg of physiological saline was given orally and animals were housed in a metabolism cage, and urine was collected at 3-hr intervals for 6 hrs. The experiments were conducted in 3 groups (3 rats/group) per test compound. Urine was measured with a measuring cylinder; urinary electrolytes ($Na^+$ and $K^+$) with a Stat/Iron system (Technicon); and urinary uric acid by a modification of Makino's method using a kit (Determiner UA, sold by Kyowa Medex. Co.). All parameters were expressed as excretion values (%) per kg of body weight in comparison with those of the control rats.

(d) Test result:

| Administered Test compound | Volume of urine (%) | Excretion of $Na^+$ (%) | Excretion of $K^+$ (%) | Excretion of uric acid (%) | $Na^+/K^+$ |
|---|---|---|---|---|---|
| — (control) | 100 | 100 | 100 | 100 | 1.00 |
| 1 | 272 | 382 | 162 | 171 | 2.44 |
| 2 | 190 | 364 | 189 | 163 | 1.94 |
| 3 | 113 | 250 | 110 | 222 | 2.32 |
| 4 | 244 | 212 | 87 | 181 | 2.58 |
| 5 | 290 | 308 | 142 | 170 | 1.99 |

The object compound (I) or its pharmaceutically acceptable salt can usually be administered to mammals including human beings in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

A dosage of the present active ingredient is to be varied depending on various factors such as weight and/or age of a patient and/or the kind of the diseases, and further the kind of administration route. In general, an effective dosage can be selected from a range of about 20–2000 mg/day for an oral route, about 2.5–250 mg/day for an intramuscular or intravenous injection. The total daily amount mentioned above may be divisionally given to the patient at the interval of 6–12 hours per day. Preferable single dose of the present active ingredient may be, for example, about 10–500 mg per tablet or capsule, about 1.25–250 mg per vial or ampoule, and so on.

The starting compound (II) to be used in the preparation of the object compound (I) of this invention can be specifically prepared in the following Preparations.

Preparation 1

A solution of 6-chloro-3,4-dihydro-4-oxo-2H-1-benzopyran (3.285 g), N,N-dimethylformamide dimethyl acetal (8.568 g), and triethylamine (2.727 g) in benzene (36 ml) was refluxed with stirring for 1 hour and then about three-fourths of the solvent was distilled slowly at atmospheric pressure over a period of approximately 1 hour. To the residue was added benzene (36 ml) and the solvent was distilled again. The residue was dissolved in a mixture of chloroform and ethyl acetate, treated with activated charcoal, and evaporated in vacuo. The residual solid was washed with a mixture of diethyl ether and ethyl acetate to give 6-chloro-3,4-dihydro-3-dimethylaminomethylene-4-oxo-2H-1-benzopyran (2.73 g).

IR (Nujol) : 1640, 1600, 1580, 1550 cm$^{-1}$

NMR (CDCl$_3$, δ) : 3.12 (6H, s), 5.23 (2H, s), 6.83 (1H, d, J=8 Hz), 7.30 (1H; d,d; J=2, 8 Hz), 7.58 (1H, s), 7.90 (1H, d, J=2 Hz)

Preparation 2

A solution of 6-chloro-4-oxo-1-propionyl-1,2,3,4-tetrahydroquinoline (2 g), N,N-dimethylformamide dimethyl acetal (7.009 g), and triethylamine (0.87 g) in benzene (50 ml) was refluxed with stirring for 1 hour and then about three-fourths of the solvent was distilled slowly at atmospheric pressure over a period of approximately 1 hour. To the residue was added benzene (100 ml) and the solvent was distilled again. The resulting solid was collected by filtration, washed with diethyl ether, and dried to give 6-chloro-3-dimethylaminomethylene-4-oxo-1-propionyl-1,2,3,4-tetrahydroquinoline (2.02 g).

IR (Nujol) : 1658, 1637, 1600, 1577, 1545, 1377, 1198 cm$^{-1}$

NMR (CDCl$_3$, δ) : 1.13 (3H, t, J=7.6 Hz), 2.48 (2H, q, J=7.6 Hz), 3.23 (6H, s), 4.97 (2H, s), 7.13 (1H, d, J=8.4 Hz), 7.42 (1H; d,d; J=2, 8.4 Hz), 7.62 (1H, s), 7.97 (1H, d, J=2 Hz)

Preparation 3

The following compounds were prepared in a similar manner to those of Preparation 1-2
(1) 6-Chloro-3-dimethylaminomethylene-1-ethylcarbamoyl-4-oxo-1,2,3,4-tetrahydroquinoline
  IR (Nujol) : 3280, 1660, 1655 (shoulder), 1645 (shoulder), 1600, 1570, 1540 (broad) cm$^{-1}$
(2) 6-Chloro-3-dimethylaminomethylene-1-ethoxycarbonyl-4-oxo-1,2,3,4-tetrahydroquinoline
  IR (Nujol) : 1700, 1645, 1600, 1580, 1560 cm$^{-1}$
  NMR (CDCl$_3$, δ) : 1.30 (3H, t, J=7 Hz), 3.20 (6H, s), 4.26 (2H, q, J=7 Hz), 4.89 (2H, s), 7.20-7.50 (2H, m), 7.59 (1H, s), 7.96 (1H, d, J=2 Hz)
(3) 6-Chloro-3-dimethylaminomethylene-4-oxo-1,2,3,4-tetrahydroquinoline
  IR (Nujol) : 3300, 1640, 1615 cm$^{-1}$
  NMR (DMSO-d$_6$, δ) : 3.08 (6H, s), 4.41 (2H, s), 6.36 (1H, br s), 6.62 (1H, d, J=8 Hz), 7.12 (1H; d,d; J=2, 8 Hz), 7.36 (1H, s), 7.5 (1H, d, J=2 Hz)
(4) 3-Dimethylaminomethylene-4-oxo-1-propionyl1,2,3,4-tetrahydroquinoline
  IR (Nujol) : 1655, 1650 (shoulder), 1640, 1600, 1580, 1540 (broad) cm$^{-1}$
  NMR (CDCl$_3$, δ) : 1.15 (3H, t, J=7 Hz), 2.50 (2H, q, J=7 Hz), 3.23 (6H, s), 5.0 (2H, s), 7.15-7.5 (3H, m), 7.62 (1H, s), 7.99 (1H; d,d; J=2, 8 Hz)

Preparation 4

(1) A solution of cyclopropyl-carbonyl chloride (2.09 g) in chloroform (5 ml) was added dropwise to a solution of 6-chloro-4-oxo-1,2,3,4-tetrahydroquinoline (1.815 g), N,N-dimethylaniline (2.42 g), and 4-dimethylaminopyridine (0.488 g) in chloroform (15 ml) with stirring and ice cooling over a period of 10 minutes. After being stirred overnight at ambient temperature, the mixture was washed successively with 10% hydrochloric acid, water, aqueous sodium bicarbonate, and water, dried over magnesium sulfate, and evaporated in vacuo. The residual solid was washed with diethyl ether and dried to give 6-chloro-1-cyclopropyl-carbonyl-4-oxo-1,2,3,4-tetrahydroquinoline (2.14 g).

IR (Nujol) : 1690, 1655, 1595 cm$^{-1}$

NMR (CDCl$_3$, δ) : 0.71-1.40 (4H, m), 1.68-2.23 (1H, m), 2.78 (2H, t, J=6 Hz), 4.28 (2H, t, J=6 Hz), 7.5 (2H, s), 7.92-8.05 (1H, m)

(2) A solution of 6-chloro-1-cyclopropyl-carbonyl-4-oxo-1,2,3,4-tetrahydroquinoline (1.996 g), N,N-dimethylformamide dimethyl acetal (3.808 g), and triethylamine (1.212 g) in benzene (16 ml) was refluxed with stirring for 30 minutes and then about three-fourths of the solvent was distilled slowly at atmospheric pressure over a period of approximately 30 minutes. To the residue was added benzene (16 ml) and the solvent was distilled again. The residue was dissolved in ethyl acetate, treated with activated charcoal, and evaporated in vacuo. The residual solid was washed with diethyl ether to give 6-chloro-1-cyclopropyl-carbonyl-3-dimethylaminomethylene-4-oxo-1,2,3,4-tetrahydroquinoline (2.43 g).

IR (Nujol) : 1665, 1640, 1600, 1570, 1550 cm$^{-1}$

NMR (CDCl$_3$, δ) : 0.72-1.02 (2H, m), 1.02-1.26 (2H, m), 1.78-2.06 (1H, m), 3.22 (6H, s), 5.02 (2H, s), 7.42 (2H, m), 7.66 (1H, s), 8.01 (1H, m)

Preparation 5

(1) The following compound was prepared in a similar manner to that of Preparation 4 (1).
6-Nitro-4-oxo-1-propionyl-1,2,3,4-tetrahydroquinoline (10.66 g).
IR (Nujol) : 1695, 1605, 1580, 1520, 1460 (broad), 1340, 1300 cm$^{-1}$
NMR (DMSO-d$_6$, δ) : 1.11 (3H, t, J=7 Hz), 2.73 (2H, q, J=7 Hz), 2.88 (2H, t, J=6 Hz), 4.20 (2H, t, J=6 Hz), 8.1 (1H, d, J=8 Hz), 8.38 (1H; d,d; J=2, 8 Hz), 8.54 (1H, d, J=2 Hz)

(2) A mixture of 6-nitro-4-oxo-1-propionyl-1,2,3,4tetrahydroquinoline (2.976 g), N,N-dimethylformamide dimethyl acetal (8.568 g), and triethylamine (1.818 g) in benzene (24 ml) was refluxed with stirring for 2.5 hours and cooled to room temperature. The resulting precipitates were collected by filtration, washed with cold ethyl acetate, and dried to give 3-dimethylaminomethylene-6-nitro-4-oxo-1-propionyl-1,2,3,4-tetrahydroquinoline (3.345 g).

IR (Nujol) : 1670, 1645, 1610, 1585, 1545 (broad), 1510 cm$^{-1}$

NMR (DMSO-d$_6$, δ) : 1.07 (3H, t, J=7 Hz), 2.67 (2H, q, J=7 Hz), 3.23 (6H, s), 4.95 (2H, s), 7.59 (1H, s), 7.83 (1H, d, J=8 Hz), 8.30 (1H; d,d; J=2, 8 Hz), 8.56 (1H, d, J=2 Hz)

Preparation 6

(1) Propionylchloride (2.99 ml) was added dropwise to a suspension of 6,7-dichloro-4-oxo-1,2,3,4-tetrahydroquinoline (3.70 g) in pyridine (2.76 ml) and benzene (40.0 ml). After the mixture was stirred at room temperature for 1 hour, water (50 ml) and ethylacetate (10 ml) was added to the mixture. The organic layer was washed with diluted hydrochloric acid, diluted aqueous sodium hydrogen carbonate, brine and dried over magnesium sulfate. The solvent was evaporated in vacuo to give light brown powder (4.60 g), which was recrystallized from a mixture of ethyl acetate and n-hexane to give 6,7-dichloro-4-oxo-1-propionyl-1,2,3,4-tetrahydroquinoline (3.85 g) as slighthly brown prisms.

mp : 135° to 137° C.

IR (Nujol) : 1670 cm$^{-1}$

NMR (CDCl$_3$, δ) : 1.26 (3H, t, J=8 Hz), 2.63 (2H, q, J=8 Hz), 2.79 (3H, t, J=6 Hz), 4.19 (3H, t, J=6 Hz), 7.93 (1H, s), 8.02 (1H, s)

(2) The following compound was prepared in a similar manner to that of Preparation 1.
6,7-Dichloro-3-dimethylaminomethylene-4-oxo-1-propionyl-1,2,3,4-tetrahydroquinoline mp : 182° to 184° C. (recrystallized from ethanol)

IR (Nujol) : 1650 cm$^{-1}$

NMR (CDCl$_3$, δ) : 1.16 (3H, t, J=7 Hz), 2.48 (2H, q, J=7 Hz), 3.18 (6H, s), 4.94 (2H, s), 7.36 (1H, s), 7.58 (1H, s), 8.02 (1H, s)

Preparation 7

(1) The following compound was prepared in a similar manner to that of Preparation 4 (1).
6-Methoxy-4-oxo-1-propionyl-1,2,3,4-tetrahydroquinoline
IR (Nujol) : 1685, 1655 (shoulder), 1645, 1605, 1575, 1490 cm$^{-1}$ NMR (CDCl$_3$, δ) : 1.21 (3H, t, J=7 Hz), 2.57 (2H, q, J=7 Hz), 2.76 (2H, t, J=6 Hz), 3.85 (3H, s), 4.20 (2H, t, J=6 Hz), 7.11 (1H; d,d; J=2, 8 Hz), 7.28-7.56 (2H, m)

(2) The following compound was prepared in a similar manner to that of Preparation 1.

3-Dimethylaminomethylene-6-methoxy-4-oxo-1-propionyl-1,2,3,4-tetrahydroquinoline (2.12 g)

IR (Nujol) : 1655, 1635, 1605, 1580, 1560 (shoulder), 1550 cm$^{-1}$

NMR (CDCl$_3$, δ) : 1.13 (3H, t, J=7 Hz), 2.45 (2H, q, J=7 Hz), 3.23 (6H, s), 3.87 (3H, s), 4.99 (2H, s), 6.99 (1H; d,d; J=3, 8 Hz), 7.15 (1H, d, J=8 Hz), 7.53 (1H, d, J=3 Hz), 7.64 (1H, s)

Preparation 8

(1) The following compound was prepared in a similar manner to that of Preparation 4 (1).

6-Chloro-1-myristoyl-4-oxo-1,2,3,4-tetrahydroquinoline

IR (Nujol) : 1690, 1660, 1655 (shoulder), 1595 cm$^{-1}$

NMR (CDCl$_3$, δ) : 0.88 (3H, t, J=7 Hz), Ca. 1.1–1.9 (22H, m), 2.57 (2H, t, J=6 Hz), 2.77 (2H, t, J=6 Hz), 4.21 (2H, t, J=6 Hz), 7.52 (2H, br s), 7.97 (1H, br s)

(2) The following compound was prepared in a similar manner to that of Preparation 1.

6-Chloro-3-dimethylaminomethylene 1-myristoyl-4-oxo-1,2,3,4-tetrahydroquinoline

IR (Nujol) : 1665, 1645, 1600, 1570, 1545 (broad) cm$^{-1}$

NMR (CDCl$_3$, δ) : 0.88 (3H, t, J=6 Hz), Ca. 1.0–1.8 (22H, m), 2.44 (2H, t, J=7 Hz), 3.22 (6H, s), 4.96 (2H, s), 7.14 (1H, d, J=8 Hz), 7.39 (1H; d,d; J=2, 8 Hz), 7.61 (1H, s), 7.96 (1H, d, J=2 Hz)

Preparation 9

(1) The following compound was prepared in a similar manner to that of Preparation 4 (1).

6-Chloro-1-mesyl-4-oxo-1,2,3,4-tetrahydroquinoline

IR (Nujol) 1690, 1595 cm$^{-1}$

NMR (CDCl$_3$, δ) : 2.83 (2H, t, J=6 Hz), 3.07 (3H, s), 4.20 (2H, t, J=6 Hz), 7.46 (1H; d,d; J=2, 9 Hz), 7.71 (1H, d, J=9 Hz), 7.97 (1H, d, J=2 Hz)

(2) The following compound was prepared in a similar manner to that of Preparation 1.

6-Chloro-3-dimethylaminomethylene-1-mesyl-4-oxo-1,2,3,4-tetrahydroquinoline

IR (Nujol) : 1650 (shoulder), 1645, 1595, 1570, 1550 cm$^{-1}$

NMR (CDCl$_3$, δ) :

2.76 (s) } (3H), 3.24 (s) } (6H), 4.92 (s) } (2H)
2.68 (s)        3.18 (s)        4.84 (s)

7.40 (1H; d,d ; J=2, 8 Hz), 7.56 (1H, d, J=8 Hz), 7.70 (1H, s), 7.98 (d, J=2Hz) } (1H)
7.91 (d, J=2Hz)

Preparation 10

(1) The following compound was prepared in a similar manner to that of Preparation 4 (1).

5,6-Dichloro-4-oxo-1-propionyl-1,2,3,4-tetrahydroquinoline mp : 122° to 123° C. (recrystallized from a mixture of ethyl acetate and n-hexane)

IR (Nujol) : 1690, 1650 cm$^{-1}$

NMR (CDCl$_3$, δ) : 1.20 (3H, t, J=7 Hz), 2.54 (2H, q, J=7 Hz), 2.84 (2H, t, J=6 Hz), 4.14 (2H, t, J=6 Hz), 7.36 (1H, d, J=8.5 Hz), 7.59 (1H, d, J=8.5 Hz)

(2) The following compound was prepared in a similar manner to that of Preparation 1.

5,6-Dichloro-3-dimethylaminomethylene-4-oxo-1-propionyl-1,2,3,4-tetrahydroquinoline mp : 219° to 220° C. (recrystallized from ethanol)

IR (Nujol) : 1660 cm$^{-1}$

NMR (DMSO-d$_6$, δ) : 1.02 (3H, t, J=7.5 Hz), 2.53 (2H, q, J=7.5 Hz), 3.17 (6H, s), 4.78 (2H, s), 7.41 (1H, d, J=9 Hz), 7.53 (1H, s), 7.69 (1H, d, J=9 Hz)

Preparation 11

(1) The following compound was prepared in a similar manner to that of Preparation 4 (1).

6,8-Dichloro-4-oxo-1-propionyl-1,2,3,4-tetrahydroquinoline

IR (Nujol) : 3500, 3275, 1670 cm$^{-1}$

NMR (CDCl$_3$, δ) : 1.18 (3H, t, J=8 Hz), 2.48 (2H, br s), 2.78 (2H, t, J=6 Hz), 3.80 (1H, br s), 4.56 (1H, br s), 7.64 (1H, d, J=2 Hz), 7.86 (1H, d, J=2 Hz)

(2) The following compound was prepared in a similar manner to that of Preparation 1.

6,8-Dichloro-3-dimethylaminomethylene-4-oxo-1-propionyl-1,2,3,4-tetrahydroquinoline mp : 125° to 127° C. (recrystallized from ether)

IR (Nujol) : 1670, 1635 cm$^{-1}$

NMR (CDCl$_3$, δ) : 1.06 (3H, t, J=8 Hz), 1.94–2.22 (1H, m), 2.34–2.64 (1H, m), 3.24 (6H, s), 3.74–4.02 (1H, m), 5.78–6.14 (1H, m), 7.50 (1H, d, J=2 Hz), 7.65 (1H, s), 7.86 (1H, d, J=2 Hz)

Preparation 12

(1) The following compound was prepared in a similar manner to that of Preparation 4 (1).

6-Methyl-4-oxo-1-propionyl-1,2,3,4-tetrahydroquinoline

IR (Nujol) : 1690, 1655 (broad), 1610 cm$^{-1}$

NMR (CDCl$_3$, δ) : 1.22 (3H, t, J=7 Hz), 2.37 (3H, s), 2.59 (2H, q, J=7 Hz), 2.75 (2H, t, J=6 Hz), 4.21 (2H, t, J=6 Hz), 7.37 (2H, br s), 7.79 (1H, br s)

(2) The following compound was prepared in a similar manner to that of Preparation 1.

3-Dimethylaminomethylene-6-methyl-4-oxo-1-propionyl-1,2,3,4-tetrahydroquinoline

IR (Nujol) : 1655, 1635, 1610, 1580, 1550 (broad) cm$^{-1}$

NMR (CDCl$_3$, δ) : 1.12 (3H, t, J=7 Hz), 2.38 (3H, s), 2.46 (2H, q, J=7 Hz), 3.22 (6H, s), 4.98 (2H, s), 7.08 (1H, d, J=8 Hz), 7.24 (1H; d,d; J=2, 8 Hz), 7.61 (1H, s), 7.80 (1H, d, J=2 Hz)

Preparation 13

(1) The following compound was prepared in a similar manner to that of Preparation 4 (1).

6-Chloro-1-(2,3-dimethylpentanoyl)-4-oxo-1,2,3,4tetrahydroquinoline (3.39 g)

IR (film/Nacl) 1680, 1660, 1590 cm$^{-1}$

NMR (CDCl$_3$, δ) : 0.56–2.13 (12H, m), 2.64–3.13 (3H, m), 3.66–4.20 (1H, m), 4.36–4.86 (1H, m), 7.33–7.66 (2H, m), 7.92–8.07 (1H, m)

(2) The following compound was prepared in a similar manner to that of Preparation 1.

6-Chloro-3-dimethylaminomethylene-1-(2,3-dimethylpentanoyl)-4-oxo-1,2,3,4-tetrahydroquinoline IR (Nujol) 1660, 1640, 1600, 1580, 1555 cm$^{-1}$ NMR (CDCl$_3$, δ) : 0.46–2.1 (12H, m), 2.81 (1H, quintet), 3.20 (6H, s), 4.51 (1H, d, J=14 Hz), 5.43 (1H; d,d; J=2, 14 Hz), 7.08 (1H, d, J=8 Hz), 7.38 (1H; d,d; J=2, 8 Hz), 7.61 (1H, s), 7.94 (1H, d, J=2 Hz)

Preparation 14

(1) The following compound was prepared in a similar manner to that of Preparation 4 (1).

6-(4-Chlorophenoxy)-4-oxo-1-propionyl-1,2,3,4-tetrahydroquinoline mp : 96° to 98° C. (recrystallized from a mixture of ethyl acetate and n-hexane)

IR (Nujol) 1685, 1655 cm$^{-1}$

NMR (CDCl$_3$, δ) : 1.23 (3H, t, J=8 Hz), 2.60 (2H, q, J=8 Hz), 2.76 (2H, t, J=6 Hz), 4.21 (2H, t, J=6 Hz), 6.90–7.62 (7H, m)

(2) The following compound was prepared in a similar manner to that of Preparation 1.

6-(4-Chlorophenoxy)-3-dimethylaminomethylene-4-oxo-1-propionyl-1,2,3,4-tetrahydroquinoline mp: 146° to 148° C. (recrystallized from a mixture of ethanol and n-hexane)

IR (Nujol) : 1660, 1635 cm$^{-1}$

NMR (CDCl$_3$, δ) : 1.15 (3H, t, J=7 Hz), 2.48 (2H, q, J=7 Hz), 3.21 (6H, s), 4.98 (2H, s), 6.91–7.61 (8H, m)

Preparation 15

(1) The following compound was prepared in a similar manner to that of Preparation 4 (1).

6-Chloro-1-ethanesulfonyl 4-oxo-1,2,3,4-tetrahydroquinoline mp : 55°–68° C.

IR (Film<CHCl$_3$>) : 1685, 1350, 1150 cm$^{-1}$

NMR (CDCl$_3$, δ) : 1.41 (3H, t, J=8 Hz), 2.86 (2H, t, J=6 Hz), 3.26 (2H, q, J=8 Hz), 4.19 (2H, t, J=6 Hz), 7.50 (1H, dd, J=2 Hz, 9 Hz), 7.69 (1H, d, J=9 Hz), 8.02 (1H, d, J=2 Hz)

(2) The following compound was prepared in a similar manner to that of Preparation 1.

6-Chloro-3-dimethylaminomethylene-1-ethanesulfonyl-4-oxo-1,2,3,4-tetrahydroquinoline mp : 141° to 143° C.

IR (Nujol) : 1645, 1350, 1142 cm$^{-1}$

NMR (CDCl$_3$, δ) : 1.21 (3H, t, J=7.5 Hz), 2.94 (2H, q, J=7.5 Hz), 3.23 (6H, s), 4.94 (2H, s), 7.43 (1H, d,d, J=2 Hz, 8 Hz), 7.62 (1H, d, J=8 Hz), 7.73 (1H, s), 8.03 (1H, d, J=2 Hz)

Preparation 16

(1) A solution of methanesulfonyl chloride (2.004 g) in methylene chloride (5 ml) was added dropwise to a solution of 6-amino-4-oxo-1-propionyl-1,2,3,4-tetrahydroquinoline (1.526 g) and triethylamine (2.121 g) in methylene chloride (15 ml) with ice cooling over a period of 15 minutes and stirred for further 1 hour. The mixture was diluted with chloroform, washed successively with 10% hydrochloric acid, water, and brine, dried over magnesium sulfate, and evaporated in vacuo. The residual solid was washed with methanol and dried to give 6-(N,N-dimesylamino)-4-oxo-1-propionyl-1,2,3,4-tetrahydroquinoline (2.51 g).

IR (Nujol) : 1700, 1670, 1600, 1370, 1160 cm$^{-1}$

NMR (DMSO-d$_6$, δ) : 1.08 (3H, t, J=7 Hz), 2.67 (2H, q, J=7 Hz), 2.81 (2H, t, J=6 Hz), 3.51 (6H, s), 4.17 (2H, t, J=6 Hz), 7.68 (1H; d,d; J=2,8 Hz), 7.87 (1H, d, J=2 Hz), 7.93 (1H, d, J=8 Hz)

(2) The following compound was prepared in a similar manner to that of Preparation 1.

3-Dimethylaminomethylene-6-(N-methyl-N-mesylamino)-4-oxo-1-propionyl-1,2,3,4-tetrahydroquinoline IR (Nujol) : 1655, 1640, 1610, 1580, 1550 (broad) cm$^{-1}$ NMR (CDCl$_3$, δ) : 1.14 (3H, t, J=7 Hz), 2.51 (2H, q, J=7 Hz), 2.86 (3H, s), 3.21 (6H, s), 3.33 (3H, s) 4.98 (2H, s), 7.20 (1H, d, J=8 Hz), 7.54 (1H; d,d; J=2, 8 Hz), 7.61 (1H, s), 7.87 (1H, d, J=2 Hz)

Preparation 17

(1) A mixture of 6-methoxy-4-oxo-1-propionyl-1,2,3,4-tetrahydroquinoline (1.957 g) and aluminum chloride (3.359 g) in benzene (42 ml) was heated at 60° to 65° with stirring for 4 hours. To the aluminum chloride complex was added a mixture of crushed ice and 10% hydrochloric acid and extracted with ethyl acetate. The extract was washed with water, dried over magnesium sulfate, and evaporated in vacuo. The residue was purified by column chromatography on silica gel (30 g) with a mixture of chloroform and methanol (50:1 to 10:1) as an eluent. The eluates were evaporated in vacuo to give 6-hydroxy-4-oxo-1-propionyl-1,2,3,4-tetrahydroquinoline (1.52 g).

IR (Nujol) : 3200 (broad), 1690, 1635 (shoulder), 1620, 1610, 1590 cm$^{-1}$

NMR (DMSO-d$_6$, δ) : 1.05 (3H, t, J=7 Hz), 2.54 (2H, q, J=7 Hz), 2.69 (2H, t, J=6 Hz), 4.06 (2H, t, J=6 Hz), 7.0 (1H; d,d; J=2, 8 Hz), 7.20 (1H, d, J=2 Hz), 7.50 (1H, d, J=8 Hz), 9.72 (1H, s)

(2) A mixture of 6-hydroxy-4-oxo-1-propionyl-1,2,3,4-tetrahydroquinoline (1.314 g), methyl bromoacetate (1.01 g), and potassium carbonate (0.828 g) in N,N-dimethylformamide (10 ml) was stirred at room temperature for 24 hours, poured into water, and extracted with ethyl acetate. The extract was washed with water, dried over magnesium sulfate, and evaporated in vacuo. The residue was purified by column chromatography on silica gel (15 g) with chloroform as an eluent to give 6-methoxycarbonylmethoxy-4-oxo-1-propionyl-1,2,3,4-tetrahydroquinoline (2.08 g).

IR (Nujol) : 1740, 1690, 1655 (shoulder), 1650 cm$^{-1}$

NMR (CDCl$_3$, δ) : 1.22 (3H, t, J=7 Hz), 2.61 (2H, q, J=7 Hz), 2.78 (2H, t, J=6 Hz), 3.83 (3H, s), 4.24 (2H, t, J=6 Hz), 4.70 (2H, s), 7.20 (1H; d,d; J=2, 8 Hz), 7.47 (1H, d, J=2 Hz), 7.55 (1H, d, J=8 Hz)

(3) The following compound was prepared in a similar manner to that of Preparation 1.

3-Dimethylaminomethylene-6-methoxycarbonylmethoxy-4-oxo-1-propionyl-1,2,3,4-tetrahydroquinoline IR (Nujol) : 1735, 1655, 1640 (shoulder), 1630, 1600, 1580, 1540 cm$^{-1}$ NMR (DMSO-d$_6$, δ) : 0.99 (3H, t, J=7 Hz), 2.47 (2H, q, J=7 Hz), 3.28 (6H, s), 3.71 (3H, s), 4.84 (4H, s), 7.08 (1H; d,d; J=2, 8 Hz), 7.26 (1H, d, J=2 Hz), 7.43 (1H, d, J=8 Hz), 7.50 (1H, s)

Preparation 18

(1) A solution of 6-hydroxy-4-oxo-1-propionyl-1,2,3,4-tetrahydroquinoline (1.643 g) and N-chlorosuccinimide (1.068 g) in N,N-dimethylformamide (10 ml) was stirred at room temperature for 18 hours, poured into water, and extracted with ethyl acetate. The extract was washed with water, dried over magnesium sulfate, and evaporated in vacuo. The residual solid was recrystallized from chloroform to give 5-chloro-6-hydroxy-4-oxo-1-propionyl-1,2,3,4-tetrahydroquinoline (1.74 g).

IR (Nujol) : 3240, 1695, 1630, 1565 cm$^{-1}$

NMR (DMSO-d$_6$, δ) : 1.02 (3H, t, J=7 Hz), 2.52 (2H, q, J=7 Hz), 2.76 (2H, t, J=6 Hz), 4.03 (2H, q, J=6 Hz), 7.17 (1H, d, J=8 Hz), 7.40 (1H, d, J=8 Hz), 10.32 (1H, s)

(2) The following compound was prepared in a similar manner to that of Preparation 17 (2).

5-Chloro-6-methoxycarbonylmethoxy-4-oxo-1-propionyl-1,2,3,4-tetrahydroquinoline

IR (Nujol) : 1765, 1695, 1660, 1600 cm$^{-1}$

NMR (CDCl$_3$, δ) : 1.17 (3H, t, J=7 Hz), 2.51 (2H, q, J=7 Hz), 2.83 (2H, t, J=6 Hz), 3.79 (3H, s), 4.13 (2H, t, J=6 Hz), 4.73 (2H, s), 7.06 (1H, d, J=9 Hz), 7.31 (1H, d, J=9 Hz)

(3) The following compound was prepared in a similar manner to that of Preparation 1.

5-Chloro-3-dimethylaminomethylene-6-methoxycarbonylmethoxy-4-oxo-1-propionyl-1,2,3,4-tetrahydroquinoline IR (Nujol) : 1760, 1660, 1640, 1600, 1550 cm$^{-1}$ NMR (CDCl$_3$, δ) : 1.13 (3H, t, J=7 Hz), 2.45 (2H, q, J=7 Hz), 3.20 (6H, s), 3.82 (3H, s), 4.73 (2H, s), 4.88 (2H, s), 7.03 (2H, s), 7.63 (1H, s)

Preparation 19

(1) A solution of 6-nitro-4-oxo-1-propionyl-1,2,3,4-tetrahydroquinoline (6.076 g) in methanol (60 ml) was hydrogenated over 5% palladium on carbon (0.5 g) under atmospheric pressure at ambient temperature. After the theoretical amount of hydrogen gas was absorbed, the catalyst was filtered off and the filtrate was evaporated in vacuo. The residual solid was washed with diethyl ether and dried to give 6-amino-4-oxo-1-propionyl-1,2,3,4-tetrahydroquinoline (4.815 g).

IR (Nujol) : 3450, 3350, 1690 (shoulder), 1680, 1650, 1630, 1610 cm$^{-1}$

NMR (DMSO-d$_6$, δ) : 1.03 (3H, t, J=7 Hz), Ca. 2.3-2.8 (4H, m), 4.03 (2H, t, J=6 Hz), 5.27 (2H, br s), 6.79 (1H; d,d; J=2, 8 Hz), 7.03 (1H, d, J=2 Hz), 7.31 (1H, d, J=8 Hz)

(2) A solution of acetyl chloride (0.604 g) in methylene chloride (5 ml) was added dropwise to a solution of 6-amino-4-oxo-1-propionyl-1,2,3,4-tetrahydroquinoline (1.526 g) and N,N-dimethylaniline (1.016 g) in methylene chloride (15 ml) with ice cooling over a period of 10 minutes and stirred for further 20 minutes. The mixture was diluted with chloroform, washed successively with 10% hydrochloric acid, water, and brine, dried over magnesium sulfate, and evaporated in vacuo. The residual solid was recrystallized from methanol to give 6-acetamido-4-oxo-1-propionyl-1,2,3,4-tetrahydroquinoline (1.64 g).

IR (Nujol) : 3300, 1695, 1640 (broad), 1590 cm$^{-1}$

NMR (DMSO-d$_6$, δ) : 1.07 (3H, t, J=7 Hz), 2.05 (3H, s), 2.60 (2H, q, J=7 Hz), 2.76 (2H,, t, J=6 Hz), 4.12 (2H, t, J=6 Hz), 7.61 (1H, d, J=8 Hz), 7.79 (1H; d,d; J=2, 8 Hz), 8.12 (1H, d, J=2 Hz), 10.09 (1H, br s)

(3) The following compound was prepared in a similar manner to that of Preparation 1.

6-Acetamido-3-dimethylaminomethylene-4-oxo-1-propionyl-1,2,3,4-tetrahydroquinoline.

IR (Nujol) : 3250, 1675, 1665, 1640, 1585, 1540 (shoulder), 1535 cm$^{-1}$

NMR (DMSO-d$_6$, δ) : 1.0 (3H, t, J=7 Hz), 2.04 (3H, s), 2.48 (2H, q, J=7 Hz), 3.17 (6H, s), 4.86 (2H, s), 7.36 (1H, d, J=8 Hz), 7.48 (1H, s), 7.74 (1H; d,d; J=2, 8 Hz), 7.97 (1H, d, J=2 Hz), 10.03 (1H, br s)

Preparation 20

(1) A solution of propionyl chloride (1.018 g) in chloroform (5 ml) was added dropwise to a solution of 6-hydroxy-4-oxo-1-propionyl-1,2,3,4-tetrahydroquinoline (1.09 g), N,N-dimethylaniline (1.513 g), and 4-dimethylaminopyridine (0.061 g) in chloroform (20 ml) with stirring and ice cooling over a period of 10 minutes. After being stirred overnight at ambient temperature, the mixture was evaporated in vacuo and the residue was dissolved in ethyl acetate. The solution was washed successively with 5% hydrochloric acid, water, aqueous sodium bicarbonate, and water, dried over magnesium sulfate, and evaporated in vacuo to give an oil of 4-oxo-1-propionyl-6-propionyloxy-1,2,3,4-tetrahydroquinoline (1.51 g).

IR (film/NaCl) : 1750, 1680, 1655, 1600 cm$^{-1}$

NMR (CDCl$_3$, δ) : 1.21 (3H, t, J=7 Hz), 1.26 (3H, t, J=7 Hz), 2.59 (4H, q, J=7 Hz), 2.76 (2H, t, J=6 Hz), 4.20 (2H, t, J=6 Hz), 7.18 (1H; d,d; J=2, 8 Hz), 7.53 (1H, d, J=8 Hz), 7.66 (1H, d, J=2 Hz)

(2) The following compound was prepared in a similar manner to that of Preparation 1

3-Dimethylaminomethylene-4-oxo-1-propionyl-6-propionyloxy-1,2,3,4-tetrahydroquinoline (1.75 g)

IR (film/NaCl) : 1750, 1660, 1620 (broad) cm$^{-1}$

NMR (DMSO-d$_6$, δ) : 0.97 (6H, t, J=7 Hz), 2.40 (4H, b.q., J=7 Hz), 3.15 (6H, s), 4.83 (2H, s), 6.84 (1H; d,d; J=2,8 Hz), 7.15 (1H, d, J=2 Hz), 7.23 (1H, d, J=8 Hz), 7.43 (1H, s)

Preparation 21

A solution of 6-hydroxy-4-oxo-1-propionyl-1,2,3,4-tetrahydroquinoline (0.219 g), N,N-dimethylformamide dimethyl acetal (0.476 g), triethylamine (0.202 g) in benzene (4 ml) was refluxed with stirring for 2.5 hours and then about three-fourths of the solvent was distilled slowly at atmospheric pressure. To the residue was added a small volume of benzene and the solvent was distilled again. The resulting solid was collected by filtration to give crude product.

The crude product was chromatographed on silica gel (10 g) with chloroform and then the column was eluted with a mixture of chloroform and methanol (30:1) as eluents to give two fractions. The first fraction was evaporated in vacuo to give 3-dimethylaminomethylene-6-methoxy-4-oxo-1-propionyl-1,2,3,4-tetrahydroquinoline (0.09 g).

The physical data of the compound was identical to that of the object compound of Preparation 7 (2).

The second fraction was evaporated in vacuo to give 3-dimethylaminomethylene-6-hydroxy-4-oxo-1-propionyl-1,2,3,4-tetrahydroquinoline (0.19 g).

IR (Nujol) : 3100 (broad), 1660, 1610, 1540 (broad) cm$^{-1}$

NMR (DMSO-d$_6$, δ) : 0.99 (3H, t, J=7 Hz), 2.43 (2H, q, J=7 Hz), 3.18 (6H, s), 4.85 (2H, s), 6.88 (1H, d,d; J=2, 8 Hz), 7.20 (1H, d, J=2 Hz), 7.28 (1H, d, J=8 Hz), 7.48 (1H, s), 9.56 (1H, s)

Preparation 22

The following compound was prepared in a similar manner to that of Preparation 1-2.

6-Chloro-3-dimethylaminomethylene-1-methyl-4-oxo-1,2,3,4-tetrahydroquinoline m.p. 122° to 125° C. (recrystallized from a mixture of benzene and n-hexane)

IR (Nujol) : 1635 cm$^{-1}$

NMR (DMSO-d$_6$, δ) : 2.80 (3H, s), 3.07 (6H, s), 4.30 (2H, s), 6.61 (1H, d, J=9 Hz), 7.23 (1H, d,d, J=9 Hz and 2 Hz), 7.38 (1H, s) and 7.57 (1H, d, J=2 Hz)

Preparation 23

(1) The following compound was prepared in a similar manner to that of Preparation 4 (1).

6-Chloro-1-(3-methoxypropionyl)-4-oxo-1,2,3,4-tetrahydroquinoline m.p. : 91° to 93° C. (recrystallized from a mixture of ethyl acetate and n-hexane).

IR (Nujol) : 1655 (br.) cm$^{-1}$

NMR (CDCl$_3$, δ) : 2.76 (2H, t, J=6.5 Hz), 2.79 (2H, t, J=6.5 Hz), 3.32 (3H, s), 3.71 (2H, t, J=6.5 Hz), 4.23 (2H, t, J=6.5 Hz), 7.52 (1H, d, J=2 Hz), 7.58 (1H, s) and 7.95 (1H, d, J=2 Hz)

(2) The following compound was prepared in a similar manner to that of Preparation 1-2.

6-Chloro-3-dimethylaminomethylene-1-(3-methoxypropionyl)-4-oxo-1,2,3,4-tetrahydroquinoline IR (Nujol) : 1640 (shoulder), 1626, 1583, 1559, 1530 cm$^{-1}$ NMR (CDCl$_3$, δ) : 2.70 (2H, t, J=6 Hz), 3.17 (6H, s), 3.25 (3H, s), 3.57 (2H, t, J=6 Hz), 4.87 (2H, s), 7.48 (1H, s), 7.50 (1H, d, J=2 Hz), 7.52 (1H, s) and 7.68 (1H, d, J=2 Hz)

Preparation 24

A mixture of 6-chloro-4-oxo-1-propionyl-1,2,3,4-tetrahydroquinoline (200.5 g) and 1,5-diazabicyclo[5,4,0]undecene-5 (384.9 g) in ethyl formate (400.9 g) was heated at 55° C. with stirring for 7 hours and then diluted with cold water (450 ml). The mixture was washed successively with diisopropyl ether and ethyl acetate and then the aqueous layer was acidified with hydrochloric acid under ice cooling. The resultant precipitate was collected by filtration and dried to give 6-chloro-3-hydroxymethylene-4-oxo-1-propionyl-1,2,3,4-tetrahydroquinoline (168.29 g).

IR(Nujol): 3350, 1680 cm$^{-1}$

NMR(CDCl$_3$, δ): 1.20(3H, t, J=7 Hz), 2.53 (2H, q, J=7 Hz), 4.63 (2H, s), 7.20–8.30(4H, m), 9.43(1H, br s).

The filtrate was extracted with ethyl acetate and the extract was washed with water, dried over magnesium sulfate and evaporated in vacuo. To the residue was added diisopropyl ether and the mixture was stirred at room temperature for 10 minutes. The resultant powder was collected by filtration and dried to give 6-chloro-1-formyl-3-hydroxymethylene-4-oxo-1,2,3,4-tetrahydroquinoline(6 g).

IR(Nujol): 1690, 1680, 1460, 1200, 830 cm$^{-1}$

NMR(DMSO-d$_6$, δ): 4.70(2H, s), 7.50–8.26(4H, m), 8.80(1H,s)

The following Examples are given for the purpose of illustrating this invention.

EXAMPLE 1

A solution of 6-chloro-3,4-dihydro-3-dimethylaminomethylene-4-oxo-2H-1-benzopyran (1.188 g), hydrazine hydrate (0.325 g), and acetic acid (0.39 g) in a mixture of chloroform (10 ml) and methanol (20 ml) was stirred overnight at room temperature and then evaporated in vacuo. The residual solid was washed with water, dried, and recrystallized form ethyl acetate to give 8-chloro-1,4-dihydro-[1]-benzopyrano[4,3-c]pyrazole (0.95 g).

m.p. 175 to 176° C. (recrystallized from ethyl acetate)

IR (Nujol) : 3100, 1590, 1460, 1385, 1380, 1360 cm$^{-1}$

NMR (DMSO-d$_6$, δ) : 5.32 (2H, s), 6.92 (1H, d, J=9 Hz), 7.21 (1H, d,d; J=2,9 Hz), 7.59 (1H, d, J=2 Hz), 7.62 (1H, s), 13.03 (1H, br s)

EXAMPLE 2

A solution of 6-chloro-3,4-dihydro-3-dimethylaminomethylene-4-oxo-2H-1-benzopyran (1.425 g), methylhydrazine (0.359 g), and acetic acid (0.468 g) in a mixture of chloroform (10 ml) and methanol (20 ml) was stirred overnight at room temperature and then evaporated in vacuo. To the residue was added ethyl acetate, washed successively with aqueous sodium bicarbonate, water, and brine, dried over magnesium sulfate, and evaporated in vacuo.

The residual solid was recrystallized from diisopropyl ether to give 8-chloro-1-methyl-1,4-dihydro-[1]-benzopyrano[4,3-c]pyrazole (0.92 g).

mp : 80.5° to 81° C. (recrystallized from diisopropyl ether)

IR (Nujol) : 1525, 1460, 1420, 1380, 1370, 1330 cm$^{-1}$

NMR (CDCl$_3$, δ) : 4.13 (3H, s), 5.22 (2H, s), 6.90 (1H, d, J=8 Hz), 7.15 (1H; d,d; J=2, 8 Hz), 7.26 (1H, s), 7.45 (1H, d, J=2 Hz)

EXAMPLE 3

A solution of 6-chloro-3-dimethylaminomethylene-4-oxo-1-propionyl-1,2,3,4-tetrahydroquinoline (19.0 g), methylhydrazine (5.13 ml) and acetic acid (11.1 ml) in a mixture of methanol (700 ml) and tetrahydrofuran (700 ml) was stirred for 16 hours at room temperature. After acetic acid (5.0 ml) was added to the reaction solution, the solvent was evaporated in vacuo. Saturated aqueous sodium hydrogen carbonate (200 ml) was added to the residue and the mixture was extracted with ethyl acetate (200 ml). The extract was washed twice with water (100 ml), dried over magnesium sulfate and evaporated in vacuo to give yellow powder (17.8 g), which was recrystallized from a mixture of ethyl acetate and n-hexane to give 8-chloro-4,5-dihydro-1-methyl-5-propionyl-1H-pyrazolo[4,3-c]quinoline (14.7 g) as slightly yellow prisms mp : 129° to 130° C.

IR (Nujol) : 1665 cm$^{-1}$

NMR (CDCl$_3$, δ) : 1.10 (3H, t, J=7 Hz), 2.44 (2H, q, J=7 Hq), 4.13 (3H, s), 4.78 (2H, s), 7.28 (1H, d, J=2 Hz), 7.30 (1H, s), 7.33 (1H, s), 7.55 (1H, d, J=2 Hz)

EXAMPLE 4

A solution of methylhydrazine (0.331 g) in chloroform (30 ml) was added to a mixture of 3-dimethylaminomethylene-6-nitro-4-oxo-1-propionyl-1,2,3,4tetrahydroquinoline (1.818 g) and acetic acid (0.468 g) in methanol (30 ml) and stirred at room temperature for 24 hours. To the mixture was added acetic acid (2 ml) and evaporated in vacuo. The residual solid was washed with ethyl acetate to give the object compound (1.06 g).

The washings were evaporated in vacuo and the residue was purified by column chromatography on silica gel (30 g) with chloroform as an eluent to give fractions containing the object compound.

The fractions were combined and concentrated in vacuo to give a solid and the solid was recrystallized from a mixture of chloroform and ethyl acetate to give 4,5-dihydro-1-methyl-8-nitro-5-propionyl-1H-pyrazolo[4,3-c]quinoline (1.395 g).

mp : 180.5° to 182.5° C.

IR (Nujol) : 1665, 1510, 1340 cm$^{-1}$

NMR (DMSO-d$_6$, δ) : 1.02 (3H, t, J=7 Hz), 2.57 (2H, q, J=7 Hz), 4.21 (3H, s), 4.86 (2H, s), 7.50 (1H, s), 7.86

(1H, d, J=8 Hz), 8.23 (1H; d,d; J=2, 8 Hz), 8.51 (1H, d, J=2 Hz)

EXAMPLE 5

Chloroform (50 ml) was added to a mixture of 3-dimethylaminomethylene-6-nitro-4-oxo-1-propionyl-1,2,3,4-tetrahydroquinoline (3.03 g), hydrazine hydrate (0.6 g), and acetic acid (0.78 g) in methanol (50 ml) and stirred at room temperature for 8 hours. To the mixture was added acetic acid (2 ml) and evaporated in vacuo. The residual solid was washed with water, dried, and recrystallized from a mixture of chloroform and methanol to give 4,5-dihydro-8-nitro-5-propionyl-1H-pyrazolo[4,3-c]quinoline (2.53 g).

mp : 219° to 221° C.

IR (Nujol) : 3260, 1665, 1615, 1595, 1515, 1340 cm$^{-1}$

NMR (DMSO-d$_6$, δ) : 1.03 (3H, t, J=7 Hz), 2.58 (2H, q, J=7 Hz), 4.91 (2H, s), 7.72 (1H, s), 7.80 (1H, d, J=8 Hz), 8.14 (1H; d,; J=2, 8 Hz), 8.47 (1H, d, J=2 Hz), 13.14 (1H, br s)

EXAMPLE 6

A mixture of 3-dimethylaminomethylene-4-oxo-1-propionyl-1,2,3,4-tetrahydroquinoline (2.838 g), hydrazine hydrate (0.66 g), and acetic acid (0.792 g) in methanol (30 ml) was stirred at room temperature for 3 hours. To the mixture was added acetic acid (1 ml) and evaporated in vacuo. The residue was dissolved in ethyl acetate, washed successively with aqueous sodium bicarbonate, water, and brine, dried over magnesium sulfate, and evaporated in vacuo. The residue was recrystallized from ethyl acetate to give 4,5-dihydro-5-propionyl-1H-pyrazolo[4,3-c]quinoline (1.77 g).

mp : 129.5° to 131° C.

IR (Nujol) : 3160, 1615, 1600, 1580 cm$^{-1}$

NMR (DMSO-d$_6$, δ) : 0.97 (3H, t, J=7 Hz), 2.45 (2H, q, J=7 Hz), 4.83 (2H, s), 7.17–7.9 (5H, m), 12.95 (1H, br s)

EXAMPLE 7

The following compounds were prepared in a similar manner to those of Example 1–6

(1) 8-Chloro-4,5-dihydro-5-propionyl-1H-pyrazolo[4,3-c]quinoline mp : 201° to 203° C. (recrystallized from a mixture of chloroform, methanol, and diethyl ether)

IR (Nujol) : 3280, 1663 cm$^{-1}$

NMR (DMSO-d$_6$, δ) : 0.97 (3H, t, J=7.6 Hz), 2.46 (2H, q, J=7.6 Hz), 4.85 (2H, s), 7.30 (1H; d,d; J=1.8, 8.6 Hz), 7.57 (1H, d, J=8.6 Hz), 7.71 (1H, s), 7.74 (1H, d, J=1.8 Hz), 13.05 (1H, br s)

(2) 8-Chloro-4,5-dihydro-1-methyl-1H-pyrazolo[4,3-c]quinoline mp : 177° to 18° C. (recrystallized from a mixture of ethyl acetate and n-hexane)

IR (Nujol) : 3284, 1619 cm$^{-1}$

NMR (DMSO-d$_6$, δ) : 4.07 (3H, s), 4.48 (2H, s), 6.20 (1H, br s), 6.73 (1H, d, J=9 Hz), 7.11 (1H, d,d, J=2 Hz and 9 Hz), 7.55 (1H, d, J=2 Hz), 7.48 (1H, s)

(3) 8-Chloro-4,5-dihydro-1-isopropyl-5-propionyl-1H-pyrazolo[4,3-c]quinoline mp : 106° to 107° C. (recrystallized from a mixture of ethyl acetate and n-hexane)

IR (Nujol) : 1660, 1650 cm$^{-1}$

NMR (CDCl$_3$, δ) : 1.13 (3H, t, J=7 Hz), 1.63 (6H, d, J=7 Hz), 2.51 (2H, q, J=7 Hz), 4.85 (2H, s), 4.95 (1H, sept, J=7 Hz), 7.40 (1H, d, J=2 Hz), 7.43 (1H, s), 7.53 (1H, s), 7.62 (1H, d, J=2 Hz)

(4) 8-Chloro-4,5-dihydro-1-(2-dimethylaminoethyl)-5-propionyl-1H-pyrazolo[4,3-c]quinoline mp: 99° to 101° C. (recrystallized from a mixture of ethyl acetate and n-hexane)

IR (Nujol) : 1650 cm$^{-1}$

NMR (CDCl$_3$, δ) : 1.13 (3H, t, J=7 Hz), 2.35 (6H, s), 2.49 (2H, q, J=7 Hz), 2.90 (2H, t, J=7 Hz), 4.57 (2H, t, J=7 Hz), 4.87 (2H, s), 7.42 (1H, d, J=2 Hz), 7.43 (1H, s), 7.52 (1H, s), 7.87 (1H, d, J=2 Hz)

(5) 8-Chloro-4,5-dihydro-5-(2,3-dimethylpentanoyl)-1pyrazolo[4,3-c]quinoline mp : 169° to 170.5° C. (recrystallized from a mixture or ethyl acetate and diethyl ether)

IR (Nujol) : 3300, 1655 (shoulder), 1645 cm$^{-1}$

NMR (DMSO-d$_6$, δ) : 0.63 (3H, t, J=6 Hz), 0.68 (3H, d, J=6 Hz), 1.00 (3H, d, J=6 Hz), Ca. 0.9–1.8 (3H, m), Ca. 2.6–3.1 (1H, m), 4.41 (1H, d, J=14 Hz), 5.35 (1H, d, J=14 Hz), 7.40 (2H, br s), 7.74 (2H, br s), 13.03 (1H, br s)

(6) 8-Chloro-4,5-dihydro-5-ethanesulfonyl-1H-pyrazolo[4,3-c]quinoline mp : 159° to 161° C. (recrystallized from diethyl ether)

IR (Nujol) : 3340, 1600, 1350, 1330, 1150, 1145 cm$^{-1}$

NMR (DMSO-d$_6$, δ) : 0.92 (3H, t, J=8 Hz), 2.80 (2H, q, J=8 Hz), 4.82 (2H, s), 7.34 (1H, d,d, J=2, 9 Hz), 7.58 (1H, d, J=9 Hz), 7.77 (1H, d, J=2 Hz), 13.13 (1H, br s)

(7) 8-Chloro-4,5-dihydro-1H-pyrazolo[4,3-c]quinoline

IR (Nujol) : 3400, 3370, 3140, 1620 cm$^{-1}$

NMR (DMSO-d$_6$, δ) : 4.51 (2H, s), 6.02 (1H, br s), 6.58 (1H, d, J=8 Hz), 6.94 (1H; d,d; J=2, 8 Hz), 7.43 (2H, d, J=2 Hz), Ca. 12.8 (1H, br s)

(8) 8-Chloro-4,5-dihydro-5-myristoyl-1H-pyrazolo[4,3-c]quinoline mp : 93° to 94° C.

IR (Nujol) : 3200, 1630, 1600 cm$^{-1}$

NMR (DMSO-d$_6$, δ) : 0.86 (3H, t, J=6 Hz), 0.95–1.64 (22H, m), Ca. 2.3–2.6 (2H), 4.84 (2H, s), 7.32 (1H; d,d; J=2, 8 Hz), 7.53 (1H, d, J=8 Hz), 7.72 (2H, br s), 13.02 (1H, br s)

(9) 8-Chloro-4,5-dihydro-5-methanesulfonyl-1H-pyrazolo[4,3-c]quinoline mp : 171.5° to 172.5° C.

IR (Nujol) : 3350, 3150, 1605 cm$^{-1}$

NMR (DMSO-d$_6$, δ) : 2.61 (3H, s), 4.90 (2H, s), 7.45 (1H; d,d; J=2, 9 Hz), 7.64 (1H, d, J=9 Hz), 7.80 (1H, s), 7.88 (1H, d, J=2 Hz), Ca. 13.0 (1H, br s)

(10) 8-Chloro-4,5-dihydro-5-ethylcarbamoyl-1H-pyrazolo[4,3-c]quinoline mp : 214° to 215° C. (recrystallized from a mixture of ethanol and ethyl acetate)

IR (Nujol) 3150 (broad), 1625 (broad), 1580, 1540 cm$^{-1}$

NMR (DMSO-d$_6$, δ) : 1.03 (3H, t, J=7 Hz), 2.86-Ca. 3.3 (2H, m), 4.69 (2H, s), 6.74 (1H; b.t.; J=5 Hz), 7.23 (1H; d,d; J=2, 8 Hz), 7.43 (1H, d, J=8 Hz), 7.66 (2H, d, J=2 Hz), 13.0 (1H, br s)

(11) 8-Chloro-4,5-dihydro-5-ethoxycarbonyl-1H-pyrazolo[4,3-c]quinoline mp : 232° to 233° C. (decomp.) (recrystallized from a mixture of ethanol and ethyl acetate)

IR (Nujol) : 3300, 1695, 1605 cm$^{-1}$

NMR (DMSO-d$_6$, δ) : 1.21 (3H, t, J=7 Hz), 4.16 (2H, q, J=7 Hz), 4.81 (2H, s), 7.30 (1H; d,d; J=2, 8 Hz), 7.61 (1H, d, J=8 Hz), 7.71 (2H, br s), 13.0 (1H, br s)

(12) 8-Chloro-5-cyclopropyl-carbonyl-4,5-dihydro-1H-pyrazolo[4,3-c]quinoline mp : 191° to 193° C. (recrystallized from ethyl acetate)

IR (Nujol) : 3300, 1640, 1600 cm$^{-1}$

NMR (DMSO-d$_6$, δ) : 0.66–1.13 (4H, m), 1.63–2.1 (1H, m), 4.87 (2H, s), 7.35 (1H; d,d; J=2, 8 Hz), 7.58 (1H, d, J=8 Hz), 7.74 (2H, d, J=2 Hz), 12.96 (1H, br s)

(13) 4,5°-Dihydro-8-hydroxy-5-propionyl-1H-pyrazolo[4,3-c]quinoline mp : 245.5° to 247° C. (recrystallized from a mixture of methanol and chloroform)

IR (Nujol) : 3200 (broad), 1635 (broad) cm$^{-1}$

NMR (DMSO$_6$, δ) : 0.93 (3H, t, J=7 Hz), 2.37 (2H, q, J=7 Hz), 4.77 (2H, s), 6.68 (1H; d,d; J=2, 8 Hz), 7.15 (1H, d, J=2 Hz), 7.28 (1H, d, J=8 Hz), 7.63 (1H, br s), 9.56 (1H, br s), 12.83 (1H, br s)

(14) 4,5-Dihydro-8-(N-methyl-N-mesylamino)-5-propionyl-1H-pyrazolo[4,3-c]quinoline mp : 216° to 218° C. (recrystallized from a mixture of chloroform and methanol)

IR (Nujol) : 3240, 1625 cm$^{-1}$

NMR (DMSO-d$_6$, δ) : 1.01 (3H, t, J=7 Hz), 2.49 (2H, q, J=7 Hz), 3.0 (3H, s), 3.28 (3H, s), 4.83 (2H, s), 7.29 (1H; d,d; J=2, 8 Hz), 7.54 (1H, d, J=8 Hz), 7.66 (1H, s), 7.74 (1H, d, J=2 Hz) 13.0 (1H, br s)

(15) 4,5-Dihydro-8-methoxy-5-propionyl-1H-pyrazolo[4,3-c]quinoline mp : 132.5° to 134° C.

IR (Nujol) 3200, 1625, 1495 cm$^{-1}$

NMR (DMSO-d$_6$, δ) : 0.97 (3H, t, J=7 Hz), 2.39 (2H, q, J=7 Hz), 3.85 (3H, s), 4.83 (2H, s), 6.88 (1H; d, d; J=2, 8 Hz), 7.32 (1H, d, J=2 Hz), 7.42 (1H, d, J=8 Hz), 7.67 (1H, br s), 12.92 (1H, br s)

(16) 8Acetamido-4,5-dihydro-5-propionyl-1H-pyrazolo[4,3-c]quinoline mp : 235° to 237.5° C. (decomp.)

IR (Nujol) : 3200 (broad), 1670, 1640, 1610, 1600 cm$^{-1}$

NMR (DMSO-d$_6$, δ) : 0.97 (3H, t, J=7 Hz), 2.09 (3H, s), 2.42 (2H, q, J=7 Hz), 4.79 (2H, s), 7.39 (2H, s), 7.59 (1H, s), 8.02 (1H, d, J=2 Hz), 9.93 (1H, s), 12.93 (1H, br s)

(17) 8,9-Dichloro-4,5-dihydro-5-propionyl-1H-pyrazolo[4,3-c]quinoline mp : 179° to 180° C. (recrystallized from a mixture of ethyl acetate and n-hexane)

IR (Nujol) : 3210, 1660 cm$^{-1}$

NMR (DMSO-d$_6$, δ) : 0.97 (3H, t, J=7 Hz), 2.43 (2H, q, J=7 Hz), 4.80 (2H, s), 7.53 (2H, s), 7.75 (1H, s), 13.20 (1H,br s)

(18) 6,8-Dichloro-4,5-dihydro-5-propionyl-1H-pyrazolo[4,3-c]quinoline mp: 221° to 222° C. (recrystallized from a mixture of ethanol and n-hexane)

IR (Nujol) : 3250, 1650 cm$^{-1}$

NMR (DMSO-d$_6$, δ) : 0.96 (3H, t, J=7 Hz), 2.40 (2H, br s), 4.04 (1H, br s), 5.60 (1H, br s), 7.59 (1H, d, J=2 Hz), 7.76 (2H, s), 13.15 (1H, s)

(19) 7,8-Dichloro-4,5-dihydro-5-propionyl-1H-pyrazolo[4,3-c]quinoline mp : 245° to 246° C. (recrystallized from tetrahydrofuran)

IR (Nujol) : 3250, 1655 cm$^{-1}$

NMR (DMSO-d$_6$, δ) : 1.02 (3H, t, J=7 Hz), 2.54 (2H, q, J=7 Hz), 4.87 (2H, s), 7.73 (1H, s), 7.90 (2H, s), 13.11 (1H, s)

(20) 9-Chloro-4,5-dihydro-8methoxycarbonylmethoxy-5-propionyl-1H-pyrazolo[4,3-c]quinoline IR (Nujol) : 3250, 1765, 1650 cm$^{-1}$ NMR (DMSO-d$_6$, δ) : 0.92 (3H, t, J=7 Hz), 2.37 (2H, q, J=7 Hz), 3.73 (3H, s), 4.76 (2H, s), 4.97 (2H, s), 7.03 (1H, d, J=9 Hz), 7.46 (1H, d, J=9 Hz), 7.70 (1H, s), 13.1 (1H, br s)

(21) 4,5-Dihydro-8-methoxycarbonylmethoxy-5-propionyl-1H-pyrazolo[4,3-c]quinoline IR (Nujol) : 3325, 1740, 1640, 1620 cm$^{-1}$ NMR (DMSO-d$_6$, δ) : 0.97 (3H, t, J=7 Hz), 2.42 (2H, q, J=7 Hz), 3.76 (3H, s), 4.83 (2H, s), 4.90 (2H, s), 6.92 (1H; d,d; J=2, 9 Hz), 7.30 (1H, d, J=2 Hz), 7.49 (1H, d, J=9 Hz), 7.68 (1H, s), Ca. 13.0 (1H, br s)

(22) 4,5-Dihydro-8-methyl-5-propionyl-1H-pyrazolo[4,3-c]quinoline mp : 164.5° to 166° C. (recrystallized from ethyl acetate)

IR (Nujol) : 3230, 1655 (shoulder), 1645, 1490 cm$^{-1}$

NMR (DMSO-d$_6$, δ) : 0.97 (3H, t, J=7 Hz), 2.37 (3H, s), Ca. 2.2–2.6 (2H, m), 4.84 (2H, s), 7.12 (1H; d,d; J=2, 8 Hz), 7.38 (1H, d, J=8 Hz), 7.60 (2H, br s), 12.90 (1H, br s)

(23) 8-(4-Chlorophenoxy)-4,5-dihydro-5-propionyl-1H-pyrazolo[4,3-c]quinoline mp : 161° to 162° C. (recrystallized from a mixture of ethyl acetate and n-hexane)

IR (Nujol) : 3280, 1625 cm$^{-1}$

NMR (CDCl$_3$, δ) : 1.11 (3H, t, J=7.5 Hz), 2.46 (2H, q, J=7.5 Hz), 4.94 (2H, s), 6.87–7.48 (8H, m), 12.00 (1H, br s)

(24) 8-Chloro-4,5-dihydro-1-ethyl-5-propionyl-1H-pyrazolo[4,3-c]quinoline mp : 112° to 113° C. (recrystallized from a mixture of ethyl acetate and n-hexane)

IR (Nujol) : 1650 cm$^{-1}$

NMR (CDCl$_3$, δ) : 1.10 (3H, t, J=7.5 Hz), 1.55 (3H, t, J=6 Hz), 2.44 (2H, q, J=7.5 Hz), 4.42 (2H, q, J=6 Hz), 4.77 (2H, s), 7.30 (1H, d, J=2 Hz), 7.32 (1H, s), 7.37 (1H, s), 7.50 (1H, d, J=2 Hz)

(25) 8-Chloro-4,5-dihydro-1-(2-hydroxyethyl)-5-propionyl-1H-pyrazolo[4,3-c]quinoline mp : 145° to 147° C.

IR (Nujol) : 3325, 1660 cm$^{-1}$

NMR (CDCl$_3$, δ) : 1.10 (3H, t, J=7 Hz), 2.48 (2H, q, J=7 Hz), 3.63 (1H, br s), 4.08–4.33 (2H, m), 4.53 (2H, t, J=5 Hz), 4.80 (2H, s), 7.30 (1H, d, J=1.5 Hz), 7.32 (1H, s), 7.42 (1H, s), 7.72 (1H, d, J=1.5 Hz)

EXAMPLE 8

(1) A solution of 6-chloro-3-dimethylaminomethylene-4-oxo-1-propionyl-1,2,3,4-tetrahydroquinoline (2.00 g), 1-tert-butoxycarbonyl-1-methylhydrazine (1.50 g) and acetic acid (1.20 ml) in methanol (100 ml) and tetrahydrofuran (100 ml) was refluxed for 9 hours with stirring. 1-tert-Butoxycarbonyl-1-methylhydrazine (1.50 g) was added to the mixture and the stirring was continued for 8 hours at reflux conditions. After the solvent was evaporated in vacuo, saturated aqueous sodium hydrogen carbonate (15 ml) was added to the mixture and extracted with ethyl acetate (30 ml). The extract was washed with water, dried over magnesium sulfate and evaporated in vacuo. The residue (3.90 g) was chromatographed on silica gel by eluting with chloroform to give 3-(2-tert-butoxycarbonyl-2-methylhydrazino)methylene-6-chloro-4-oxo-1-propionyl-1,2,3,4-tetrahydroquinoline (2.10 g) as yellow amorphous.

IR (Nujol) : 1720, 1670 cm$^{-1}$

NMR (CDCl$_3$, δ) : 1.13 (3H, t, J=7.5 Hz), 1.50 (9H, s), 2.48 (2H, q, J=7.5 Hz), 3.23 (3H, s), 4.58 (2H, s), 7.05–7.15 (1H, m), 7.28 (1H, s), 7.32 (1H, d, J=2 Hz) and 7.87(1H, d, J=2 Hz)

(2) 36.7% Ethanolic hydrogen chloride (0.10 ml) was added to a solution of 3-(2-tert-butoxycarbonyl-2-methylhydrazino)methylene-6-chloro-4-oxo-1-propionyl-1,2,3,4-tetrahydroquinoline (150 mg) in ethanol (3.0 ml) at −4° C. and stirred for 1 hour at the same temperature. After the mixture was stirred at room temperature for 4 hours, 36.7% ethanolic hydrogen chloride (0.50 ml) was added to the mixture and the stirring was continued for 1.5 hours. The solvent was evaporated in vacuo and saturated aqueous sodium hydragen carbonate was added to the residue. The mixture was extracted with ethyl acetate, washed with water and dried over magnesium sulfate. The solvent was evaporated in vacuo to give light brown powder (110 mg), which was recrystallized from a mixture of ethyl acetate and n-hexane to give pure 8-chloro-4,5-dihydro- 1 methyl-5-propionyl-1H-pyrazolo[4,3-c]-quinoline mp : 127° to 128° C.

IR (Nujol) : 1665 cm$^{-1}$

NMR (CDCl$_3$, δ) : 1.10 (3H, t, J=7 Hz), 2.44 (2H, q, J=7 Hz), 4.13 (3H, s), 4.78 (2H, s), 7.28 (1H, d, J=2 Hz), 7.30 (1H, s), 7.33 (1H, s), 7.55 (1H, d, J=2 Hz)

EXAMPLE 9

Methyl iodide (1.12 ml) was added to a suspension of 8-chloro-4,5-dihydro-5-propionyl-1H-pyrazolo[4,3-c]quinoline (4.00 g) and potassium carbonate (2.24 g) in N,N-dimethylformamide (55 ml). After being stirred for 12 hours at room temperature, the mixture was allowed to warm up to 70° C. and was then stirred for an additional 1 hour.

After the solvent was evaporated in vacuo, water (100 ml) was added to the residue and the resultant mixture was extracted with ethyl acetate (40 ml). The extract was washed with water, dried over magnesium sulfate, and evaporated in vacuo to give pale yellow powder, which was recrystallized two times from a mixture of ethyl acetate and n-hexane to give 8-chloro-4,5-dihydro-2-methyl-5-propionyl-2H-pyrazolo[4,3-c]quinoline (1.70 g) as pale yellow prisms.

mp : 137° to 138° C.

IR (Nujol) : 1635 cm$^{-1}$

NMR (CDCl$_3$, δ) : 1.08 (3H, t, J=7 Hz), 2.43 (2H, q, J=7 Hz), 3.93 (3H, s), 4.87 (2H, s), 7.23 (3H, s)

EXAMPLE 10

The following compounds were prepared in a similar manner to that of Example 9.

(1) 8-Chloro-4,5-dihydro-2-ethyl-5-propionyl-2H-pyrazolo[4,3-c]quinoline mp : 115° to 116° C. (recrystallized from a mixture of ethyl acetate and n-hexane)

IR (Nujol) : 1650 cm$^{-1}$

NMR (CDCl$_3$, δ) : 1.08 (3H, t, J=7 Hz), 1.50 (3H, t, J=7 Hz), 2.42 (2H, q, J=7 Hz), 4.18 (2H, q, J=7 Hz), 4.88 (2H, s), 7.18 (1H, d, J=1.5 Hz), 7.20 (1H, s), 7.25 (1H, s), 7.85 (1H, d, J=1.5 Hz)

(2) 8-Chloro-4,5-dihydro-2-isopropyl-5-propionyl-2H-pyrazolo[4,3-c]quinoline mp : 113° to 114° C. (recrystallized from a mixture of ethyl acetate and n-hexane)

IR (Nujol) : 1650 cm$^{-1}$

NMR (CDCl$_3$, δ) : 1.17 (3H, t, J=7.5 Hz), 1.55 (6H, d, J=6 Hz), 2.45 (2H, q, J=7.5 Hz), 4.58 (1H, quint, J=6 Hz), 4.93 (2H, s), 7.25 (1H, d, J=1.5 Hz), 7.27 (1H, s), 7.33 (1H, s), 7.93 (1H, d, J=1.5 Hz)

(3) 8-Chloro-4,5-dihydro-2-allyl--5-propionyl-2H-pyrazolo[4,3-c]quinoline mp : 107° to 108° C. (recrystallized from a mixture of ethyl acetate and n-hexane)

IR (Nujol) : 1635 cm$^{-1}$

NMR (CDCl$_3$, δ) : 1.08 (3H, t, J=7 Hz), 2.48 (2H, q, J=7 Hz), 4.75–5.42 (4H, m), 4.92 (2H, s), 5.82–6.45 (1H, m), 7.25 (1H, d, J=1.5 Hz), 7.27 (1H, s), 7.32 (1H, s), 7.92 (1H, d, J=1.5 Hz)

(4) 8-Chloro-4,5-dihydro-2-propargyl-5-propionyl-2H-pyrazolo[4,3-c]quinoline mp : 111° to 112° C. (recrystallized from a mixture of ethyl acetate and n-hexane)

IR (Nujol) : 3225, 2125, 1631 cm$^{-1}$

NMR (CDCl$_3$, δ) : 1.08 (3H, t, J=7.5 Hz), 2.37 (2H, q, J=7.5 Hz), 2.53 (1H, d, J=3 Hz), 4.90 (2H, s), 4.97 (1H, d, J=3 Hz), 7.25 (1H, d, J=1.5 Hz), 7.27 (1H, s), 7.48 (1H, s), 7.83 (1H, d, J=1.5 Hz)

(5) 8-Chloro-4,5-dihydro-5-propionyl-2-(2-methoxyethyl)-2H-pyrazolo[4,3,-c]quinoline mp : 88° to 89° C. (recrystallized from a mixture of ethyl acetate and n-hexane)

IR (Nujol) : 1645 cm$^{-1}$

NMR (CDCl$_3$, δ) : 1.10 (3H, t, J=8 Hz), 2.40 (2H, q, J=8 Hz), 3.34 (3H, s), 3.78 (2H, t, J=5 Hz), 4.32 (2H, t, J=5 Hz), 4.90 (2H, s), 7.26 (1H, d, J=1.5 Hz), 7.27 (1H, s), 7.38 (1H, s), 7.89 (1H, d, J=1.5 Hz)

(6) 8-Chloro-4,5-dihydro-5-propionyl-2-(2-oxopropyl)-2H-pyrazolo[4,3-c]quinoline mp : 131° to 132° C. (recrystallized from a mixture of ethyl acetate and n-hexane)

IR (Nujol) : 1725, 1645 cm$^{-1}$

NMR (CDCl$_3$, δ) : 1.05 (3H, t, J=7 Hz), 2.13 (3H, s), 2.41 (2H, q, J=7 Hz), 4.88 (4H, s), 7.20 (1H, d, J=1.5 Hz), 7.22 (1H, s), 7.25 (1H, s), 7.78 (1H, d, J=1.5 Hz)

(7) 8-Chloro-4,5-dihydro-2-ethoxycarbonylmethyl-5-propionyl-2H-pyrazolo[4,3-c]quinoline mp : 106° to 107° C. (recrystallized from a mixture of ethyl acetate and n-hexane)

IR (Nujol) : 1750, 1635 cm$^{-1}$

NMR (CDCl$_3$, δ) : 1.10 (3H, t, J=7 Hz), 1.28 (3H, t, J=7 Hz), 2.44 (2H, q, J=7 Hz), 4.20 (2H, q, J=7 Hz), 4.92 (4H, s), 7.22 (1H, d, J=1.5 Hz), 7.23 (1H, s), 7.35 (1H, s), 7.85 (1H, d, J=1.5 Hz (8) 8-Chloro-4,5-dihydro-2-[2-(N,N-dimethylamino)-ethyl]-5-propionyl-2H-pyrazolo[4,3-c]quinoline mp : 80° to 82° C. (recrystallized from a mixture of ethyl acetate and n-hexane)

IR (Nujol) : 1655 cm$^{-1}$

NMR (CDCl$_3$, δ) : 1.10 (3H, t, J=7.5 Hz), 2.32 (6H, s), 2.43 (2H, q, J=7.5 Hz), 2.78 (2H, t, J=7 Hz), 4.23 (2H, t, J=7 Hz) 4.89 (2H, s), 7.21 (1H, d, J=1.5 Hz), 7.23 (1H, s), 7.35 (1H, s), 7.85 (1H, d, J=1.5 Hz)

(9) 8-Chloro-4,5-dihydro-5-propionyl-2-n-tetradecyl-2H-pyrazolo[4,3-c]quinoline mp : 65° to 66° C. (recrystallized from diisopropyl ether)

IR (Nujol) : 1650 cm$^{-1}$

NMR (CDCl$_3$, δ) : 0.74–2.06 (24H, m), 1.10 (3H, t, J=8 Hz), 2.39 (2H, q, J=8 Hz), 4.15 (2H, t, J=7 Hz), 4.92 (2H, s), 7.26 (1H, d, J=1.5 Hz), 7.27 (2H, s), 7.91 (1H, d, J=1.5 Hz)

(10) 2-Benzyl-8-chloro-4,5-dihydro-5-propionyl-2H-pyrazolo[4,3-c]quinoline mp : 115° to 117° C. (recrystallized from a mixture of ethyl acetate and n-hexane)

IR (Nujol) : 1650 cm$^{-1}$

NMR (CDCl$_3$, δ) : 1.10 (3H, t, J=7.5 Hz), 2.44 (2H, q, J=7.5 Hz), 4.88 (2H, s), 5.33 (2H, s), 7.25 (1H, d, J=1.5 Hz), 7.27 (2H, s), 7.35 (7H, s), 7.93 (1H, d, J=1.5 Hz)

(11) 8-Chloro-4,5-dihydro-1-allyl-5-propionyl-1H-pyrazolo[4,3-c]quinoline

NMR (CDCl$_3$, δ) : 1.10 (3H, t, J=7 Hz), 2.45 (2H, q, J=7 Hz), 4.68-5.38 (4H, m), 4.82 (2H, s), 5.77-6.40 (1H, m), 7.32 (1H, d, J=1.5 Hz), 7.33 (1H, s), 7.43 (1H, s), 7.53 (1H, d, J=1.5 Hz)

(12) 8-Chloro-4,5-dihydro-1-ethoxycarbonylmethyl-5-propionyl-1H-pyrazolo[4,3-c]quinoline NMR (CDCl$_3$, δ) : 1.13 (3H, t, J=7 Hz), 1.28 (3H, t, J=7 Hz), 2.44 (2H, q, J=7 Hz), 4.33 (2H, q, J=7 Hz), 4.87 (2H, s), 5.18 (2H, s), 7.35 (3H, s), 7.47 (1H, s)

(13) 8-Chloro-4,5-dihydro-5-propionyl-1-(2-oxopropyl)-1H-pyrazolo[4,3-c]quinoline NMR (CDCl$_3$, δ) : 1.12 (3H, t, J=7 Hz), 2.46 (2H, q, J=7 Hz), 3.35 (3H, s), 3.92 (2H, t, J=5 Hz), 4.55 (2H, t, J=5 Hz), 4.80 (2H, s), 7.30 (1H, d, J=2 Hz), 7.32 (1H, s), 7.43 (1H, s), 7.93 (1H, d, J=2 Hz)

(14) 8-Chloro-4,5-dihydro-5-propionyl-1-n-tetradecyl-1H-pyrazolo[4,3-c]quinoline NMR (CDCl$_3$, δ) : 0.73-2.10 (24H, m), 1.13 (3H, J=8 Hz), 2.42 (2H, q, J=8 Hz), 4.40 (2H, t, J=7 Hz), 4.82 (2H, s), 7.32 (1H, d), 7.37 (1H, s), 7.40 (1H, s), 7.55 (1H, d)

(15) 8-Chloro-4,5-dihydro-1-methyl-5-propionyl-1H-pyrazolo[4,3-c]quinoline

NMR (CDCl$_3$, δ) : 1.10 (3H, t, J=7 Hz), 2.44 (2H, q, J=7 Hz), 4.13 (3H, s), 4.78 (2H, s), 7.28 (1H, d, J=2 Hz), 7.30 (1H, s), 7.33 (1H, s), 7.55 (1H, d, J=2 Hz)

(16) 8-Chloro-4,5-dihydro-1-ethyl-5-propionyl-1H-pyrazolo[4,3-c]quinoline

NMR (CDCl$_3$, δ) : 1.10 (3H, t, J=7.5 Hz), 1.55 (3H, t, J=6 Hz), 2.44 (2H, q, J=7.5 Hz), 4.42 (2H, q, J=6 Hz), 4.77 (2H, s), 7.30 (1H, d, J=2 Hz), 7.32 (1H, s), 7.37 (1H, s), 7.50 (1H, d, J=2 Hz)

(17) 8-Chloro-4,5-dihydro-1-isopropyl-5-propionyl-1H-pyrazolo[4,3-c]quinoline

NMR (CDCl$_3$, δ) : 1.13 (3H, t, J=7 Hz), 1.63 (6H, d, J=7 Hz), 2.51 (2H, q, J=7 Hz), 4.85 (2H, s), 4.95 (1H, sept, J=7 Hz), 7.40 (1H, d, J=2 Hz), 7.43 (1H, s), 7.53 (1H, s), 7.62 (1H, d, J=2 Hz)

(18) 8-Chloro-4,5-dihydro-1-[2-(N,N-dimethylamino)-ethyl]-5-propionyl-1H-pyrazolo[4,3-c]quinoline NMR (CDCl$_3$, δ) : 1.13 (3H, t, J=7 Hz), 2.35 (6H, s), 2.49 (2H, q, J=7 Hz), 2.90 (2H, t, J=7 Hz), 4.57 (2H, t, J=7 Hz), 4.87 (2H, s), 7.42 (1H, d, J=2 Hz), 7.43 (1H, s), 7.52 (1H, s), 7.87 (1H, d, J=2 Hz)

EXAMPLE 11

A solution of 4,5-dihydro-8-nitro-5-propionyl-1H-pyrazolo[4,3-c]quinoline (1.36 g) in methanol (250 ml) was hydrogenated over 5% palladium on carbon (0.4 g) under atmospheric pressure at ambient temperature. After the theoretical amount of hydrogen gas was absorbed, the catalyst was filtered off and the filtrate was evaporated in vacuo. The residual solid was recrystallized from a mixture of methanol and chloroform to give 8-amino-4,5-dihydro-5-propionyl-1H-pyrazolo[4,3-c]quinoline (0.981 g).

mp : 218° to 220° C. (recrystallized from a mixture of chloroform and methanol)

IR (Nujol) : 3310, 3170 (broad), 1625 (broad) cm$^{-1}$

NMR (DMSO-d$_6$, δ) : 0.90 (3H, t, J=7 Hz), 2.34 (2H, q, J=7 Hz), 4.73 (2H, s), 5.17 (2H, s), 6.49 (1H; d,d; J=2, 8 Hz), 6.97 (1H, d, J=2 Hz), 7.1 (1H, d, J=8 Hz), 7.56 (1H, s), 12.76 (1H, br s)

EXAMPLE 12

The following compound was prepared in a similar manner to that of Example 11.

8-Amino-4,5-dihydro-1-methyl-5-propionyl-1H-pyrazolo[4,3-c]quinoline mp : 178.5° to 179/5° C.

IR (Nujol) 3380, 3340, 3220, 1650 (shoulder), 1640, 1615 cm$^{-1}$

NMR (DMSO-d$_6$, δ) : 0.91 (3H, t, J=7 Hz), 2.35 (2H, q, J=7 Hz), 4.07 (3H, s), 4.67 (2H, s), 5.28 (2H, s), 6.58 (1H; d,d; J=2, 8 Hz), 7.05 (1H, d, J=2 Hz), 7.20 (1H, d, J=8 Hz), 7.36 (1H, s)

EXAMPLE 13

A solution of sodium hydroxide (0.32 g) in water (4 ml) was added to a mixture of 4,5-dihydro-8-methoxycarbonylmethoxy-5-propionyl-1H-pyrazolo-[4,3-c]quinoline (1.26 g) in methanol (20 ml). After being stirred at room temperature for 1.5 hours, the solution was evaporated in vacuo and the residue was dissolved in an aqueous solution of sodium bicarbonate. The solution was washed with ethyl acetate and acidified with 10% hydrochloric acid under ice cooling and stirring. The resulting precipitates were collected by filtration, washed with water, and recrystallized for methanol to give 8-carboxymethoxy-4,5-dihydro-5-propionyl-1H-pyrazolo[4,3-c]quinoline (1.05 g).

mp : 207 to 208.5 (decomp.)

IR (Nujol) : 3200, 1730, 1660, 1620 cm$^{-1}$

NMR (DMSO-d$_6$, δ) : 0.96 (3H, t, J=7 Hz), 2.42 (2H, q, J=7 Hz), 4.76 (2H, s), 4.81 (2H, s), 6.87 (1H; d,d; J=3, 8 Hz), 7.26 (1H, d, J=3 Hz), 7.45 (1H, d, J=8 Hz), 7.63 (1H, s)

EXAMPLE 14

1N-Sodium hydroxide (5.00 ml) was added to a solution of 8-chloro-4,5-dihydro-2-ethoxycarbonylmethyl-5-propionyl-2H-pyrazolo[4,3-c]quinoline (1.70 g) in methanol (50.0 ml) and the mixture was stirred for 2 hours at room temperature. After the solvent was evaporated in vacuo, 1N-hydrochloric acid (15.0 ml) and ethyl acetate (5.00 ml) was added to the residue. The resultant precipitate was collected by filtration and washed with water to give white powder (1.55 g), which was recrystallized from a mixture of ethanol and n-hexane to give 8-chloro-4,5-dihydro-2-carboxymethyl-5-propionyl-2H-pyrazolo[4,3-c]quinoline (1.40 g) as colourless prisms.

mp : >125° C.

IR (Nujol) : 3360, 1720, 1630 cm$^{-1}$

NMR (DMSO-d$_6$, δ) : 0.98 (3H, t, J=8 Hz), 2.47 (2H, q, J=8 Hz), 4.86 (2H, s), 5.03 (2H, s), 7.36 (1H, dd, J=3 Hz, 9 Hz), 7.59 (1H, d, J=9 Hz), 7.69 (1H, d, J=3 Hz), 7.74 (1H, s), 11.33 (1H, br s)

EXAMPLE 15

The following compounds were prepared in a similar manner to those of Examples 1-6.

(1) 8-Chloro-4,5-dihydro-5-methyl-1H-pyrazolo[4,3-c]quinoline m.p.: 148° to 149° C. (recrystallized from a mixture of ethyl acetate and n-hexane)

IR (Nujol) : 3145 cm$^{-1}$

NMR (DMSO-d$_6$, δ) : 2.78 (3H, s), 4.35 (2H, s), 6.54 (1H, d, J=9 Hz), 7.02 (1H, d,d, J=9 Hz and 2 Hz), 7.42 (1H, s) and 7.43 (1H, d, J=2 Hz)

(2) 8-Chloro-4,5-dihydro-5-(3-methoxypropionyl)-1-methyl-1H-pyrazolo[4,3-c]quinoline m.p.: 144° to 146° C. (recrystallized from a mixture of ethyl acetate and n-hexane)

IR (Nujol) : 1647 (shoulder), 1522 cm$^{-1}$

NMR (CDCl$_3$, δ) : 2.63 (2H, t, J=6 Hz), 3.27 (3H, s), 3.50 (2H, t, J=6 Hz), 4.13 (3H, s), 4.80 (2H, s), 7.27 (1H, d, J=2 Hz), 7.28 (1H, s), 7.37 (1H, s) and 7.50 (1H, d, J=2 Hz)

(3) 8-Chloro-4,5-dihydro-1-propargyl-5-propionyl-1H-pyrazolo[4,3-c]quinoline

NMR (CDCl$_3$, δ) : 1.14 (3H, t, J=7 Hz), 2.46 (2H, q, J=7 Hz), 2.59 (1H, d, J=3 Hz), 4.86 (2H, s), 5.18 (2H, d, J=3 Hz), 7.39 (1H, d, J=1.5 Hz), 7.40 (1H, s), 7.47 (1H, s) and 7.87 (1H, d, J=1.5 Hz)

(4) 8-Chloro-5-cyclopropylcarbonyl-4,5-dihydro-1-methyl-1H-pyrazolo[4,3-c]quinoline NMR (CDCl$_3$, δ):0.62-1.13 (2H, m), 1.13-1.48 (2H, m), 1.45-2.07 (1H, m), 4.13 (3H, s), 4.82 (2H, s), 7.28 (1H, d,d, J=2.8 Hz), 7.37 (1H, s), 7.43 (1H, d, J=8 Hz) and 7.57 (1H, d, J=2 Hz)

(5) 8-Chloro-4,5-dihydro-5-mesyl-1-methyl-1H-pyrazolo [4,3-c]quinoline

NMR (CDCl$_3$, δ): 2.42 (3H, s), 4.18 (3H, s), 4.85 (2H, s), 7.48 (2H, s) and 7.73 (2H, brs)

(6) 8-Chloro-4,5-dihydro-5-ethoxycarbonyl-1-methyl-1H-pyrazolo[4,3-c]quinoline

NMR (CDCl$_3$, δ): 1.32 (3H, t, J=7 Hz), 4.17 (3H, s), 4.35 (2H, t, J=7 Hz), 4.87 (2H, s), 7.35 (1H, d, J=2 Hz), 7.37 (1H, s), 7.55 (1H, d, J=2 Hz) and 7.57 (1H, s)

(7) 8-Chloro-4,5-dihydro-5-ethylcarbamoyl-1-methyl-1H-pyrazolo [4,3-c]quinoline

NMR (CDCl$_3$, δ): 1.02 (3H, t, J=7 Hz), 2.80-3.27 (2H, m), 4.08 (3H, s), 4.58 (2H, s), 6.73 (1H, brt, J=5 Hz), 7.33 (1H, s), 7.35 (1H, d, J=2 Hz), 7.37 (1H, s) and 7.68 (1H, d, J=2 Hz)

EXAMPLE 16

The following compounds were prepared in a similar manner to that of Example 9.

(1) 8-Chloro-4,5-dihydro-1-propargyl-5-propionyl-1H-pyrazolo[4,3-c]quinoline m.p.: 148° to 149° C. (recrystallized from a mixture of ethyl acetate and n-hexane)

IR (Nujol): 3246, 2116, 1649 cm$^{-1}$

NMR (CDCl$_3$, δ): 1.14 (3H, t, J=7 Hz), 2.46 (2H, q, J=7 Hz), 2.59 (1H, d, J=3 Hz), 4.86 (2H, s), 5.18 (2H, d, J=3 Hz), 7.39 (1H, d, J=1.5 Hz), 7.40 (1H, s), 7.47 (1H, s) and 7.87 (1H, d, J=1.5 Hz)

(2) 2-(2-Butynyl)-8-chloro-4,5-dihydro-5-propionyl-2H-pyrazolo [4,3-c]quinoline m.p.: 127° to 129° C. (recrystallized from a mixture of ethyl acetate and n-hexane)

IR (Nujol): 2226, 1641 cm$^{-1}$

NMR (CDCl$_3$, δ): 1.10 (3H, t, J=7 Hz), 1.90 (3H, d, J=2 Hz), 2.44 (2H, q, J=7 Hz), 4.90 (2H, s), 4.92 (2H, q, J=2 Hz), 7.18 (1H, s), 7.20 (1H, d, J=2 Hz), 7.45 (1H, s), and 7.83 (1H, d, J=2 Hz)

(3) 8-Chloro-4,5-dihydro-5-(3-methoxypropionyl)-1-methyl-1H-pyrazolo[4,3-c]quinoline NMR (CDCl$_3$, δ): 2.63 (2H, t, J=6 Hz), 3.27 (3H, s), 3.50 (2H, t, J=6 Hz), 4.13 (3H, s), 4.80 (2H, s), 7.27 (1H, d, J=2 Hz), 7.28 (1H, s), 7.37 (1H, s) and 7.50 (1H, d, J=2 Hz)

(4) 8-Chloro-5-cyclopropylcarbonyl-4,5-dihydro-1-methyl-1H-pyrazolo[4,3,-c]quinoline NMR (CDCl$_3$, δ): 0.62-1.13 (2H, m), 1.13-1.48 (2H, m), 1.45-2.07 (1H, m), 4.13 (3H, s), 4.82 (2H, s), 7.28 (1H, d,d, J=2.8 Hz), 7.37 (1H, s), 7.43 (1H, d, J=8 Hz) and 7.57 (1H, d, J=2 Hz)

(5) 8-Chloro-4,5-dihydro-5-mesyl-1-methyl-1H-pyrazolo [4,3-c]quinoline

NMR (CDCl$_3$, δ): 2.42 (3H, s), 4.18 (3H, s), 4.85 (2H, s), 7.48 (2H, s), and 7.73 (2H, brs)

(6) 8-Chloro-4,5-dihydro-5-ethoxycarbonyl-1-methyl-1H-pyrazolo[4,3-c]quinoline

NMR (CDCl$_3$, δ): 1.32 (3H, t, J=7 Hz), 4.17 (3H, s), 4.35 (2H, t, J=7 Hz), 4.87 (2H, s), 7.35 (1H, d, J=2 Hz), 7.37 (1H, s), 7.55 (1H, d, J=2 Hz) and 7.57 (1H, s)

(7) 8-Chloro-4,5-dihydro-5-ethylcarbamoyl-1-methyl-1H-pyrazolo[4,3-c]quinoline

NMR (CDCl$_3$, δ): 1.02 (3H, t, J=7 Hz), 2.80-3.27 (2H, m), 4.08 (3H, s), 4.58 (2H, s), 6.73 (1H, brt, J=5 Hz), 7.33 (1H, s), 7.35 (1H, d, J=2 Hz), 7.37 (1H, s) and 7.68 (1H, d, J=2 Hz)

EXAMPLE 17

Cyclopropanecarbonyl chloride (1.5 ml) was added dropwise to a mixture of N,N-dimethylaniline (2.4 ml), 4-dimethylaminopyridine (5.0 mg) and 8-chloro-4,5-dihydro-1-methyl-1H-pyrazolo[4,3-c]quinoline (2.0 g) in chloroform (20 ml) at 0° C. and the mixture was allowed to stir at that temperature for 2 hours. After the solvent was evaporated in vacuo, the residue was mixed with 5% hydrochloric acid and extracted with ethyl acetate. The extract was washed with 5% hydrochloric acid, saturated aqueous sodium hydrogen carbonate and water and then dried over magnesium sulfate. The solvent was evaporated in vacuo to give light brown powder (2.0 g), which was recrystallized from a mixture of n-hexane and ethyl acetate to afford 8-chloro-5-cyclopropylcarbonyl-4,5-dihydro-1-methyl-1H-pyrazolo-[4,3-c]quinoline as colourless prisms.

m.p.: 146° to 150° C.

IR (Nujol): 1647 cm$^{-1}$

NMR (CDCl$_3$, δ): 0.62-1.13 (2H, m), 1.13-1.48 (2H, m), 1.45-2.07 (1H, m), 4.13 (3H, s), 4.82 (2H, s), 7.28 (1H, dd, J=2,8 Hz), 7.37 (1H, s), 7.43 (1H, d, J=8 Hz) and 7.57 (1H, d, J=2 Hz)

EXAMPLE 18

The following compounds were prepared in a similar manner to that of Example 17.

(1) 8-Chloro-4,5-dihydro-5-mesyl-1-methyl-1H-pyrazolo [4,3-c]quinoline m.p.: 179° to 183° C. (recrystallized from a mixture of ethyl acetate and n-hexane)

IR (Nujol): 1594, 1340, 1162 cm$^{-1}$

NMR (CDCl$_3$, δ): 2.42 (3H, s), 4.18 (3H, s), 4.85 (2H, s), 7.48 (2H, s) and 7.73 (2H, br s)

(2) 8-Chloro-4,5-dihydro-5-ethoxycarbonyl-1-methyl-1H-pyrazolo[4,3,-c]quinoline m.p.: 124° to 125° C. (recrystallized from a mixture of ethyl acetate and n-hexane)

IR (Nujol): 1686, 1600, 1523 cm$^{-1}$

NMR (CDCl$_3$, δ): 1.32 (3H, t, J=7 Hz), 4.17 (3H, s), 4.35 (2H, t, J=7 Hz), 4.87 (2H, s), 7.35 (1H, d, J=2 Hz), 7.37 (1H, s), 7.55 (1H, d, J=2 Hz) and 7.57 (1H, s)

(3) 8-Chloro-4,5-dihydro-5-ethylcarbamoyl-1-methyl-1H-pyrazolo[4,3-c]quinoline m.p.: 177° to 178° C. (recrystallized from a mixture of ethyl acetate and n-hexane)

IR (Nujol): 3306, 1635, 1598 cm$^{-1}$

NMR (DMSO-d$_6$, δ): 1.02 (3H, t, J=7 Hz), 2.80-3.27 (2H, m), 4.08 (3H, s), 4.58 (2H, s), 6.73 (1H, br t, J=5

Hz), 7.33 (1H, s), 7.35 (1H, d, J=2 Hz), 7.37 (1H, s), and 7.68 (1H, d, J=2 Hz)

(4) 8-Chloro-4,5-dihydro-1-methyl-5-propionyl-1H-pyrazolo[4,3-c]quinoline

NMR (CDCl$_3$, δ): 1.10 (3H, t, J=7 Hz), 2.44 (2H, q, J=7 Hz), 4.13 (3H, s), 4.78 (2H, s), 7.28 (1H, d, J=2 Hz), 7.30 (1H, s), 7.33 (1H, s), 7.55 (1H, d, J=2 Hz)

(5) 4,5-Dihydro-1-methyl-8-nitro-5-propionyl-1H-pyrazolo[4,3-c]quinoline

NMR (DMSO-d$_6$, δ): 1.02 (3H, t, J=7 Hz), 2.57 (2H, q, J=7 Hz), 4.21 (3H, s), 4.86 (2H, s), 7.50 (1H, s), 7.86 (1H, d, J=8 Hz), 8.23 (1H, d,d; J=2, 8 Hz), 8.51 (1H, d, J=2 Hz)

(6) 4,5-Dihydro-8-nitro-5-propionyl-1H-pyrazolo[4,3-c]quinoline

NMR (DMSO-d$_6$, δ): 1.03 (3H, t, J=7 Hz), 2.58 (2H, q, J=7 Hz), 4.91 (2H, s), 7.72 (1H, s), 7.80 (1H, d, J=8 Hz), 8.14 (1H, d, J=2, 8 Hz), 8.47 (1H, d, J=2 Hz), 13.14 (1H, br s)

(7) 4,5-Dihydro-5-propionyl-1H-pyrazolo[4,3-c]quinoline

NMR (DMSO-d$_6$, δ): 0.97 (3H, t, J=7 Hz), 2.45 (2H, q, J=7 Hz), 4.83 (2H, s), 7.17–7.9 (5H, m), 12.95 (1H, br s)

(8) 8-Chloro-4,5-dihydro-5-propionyl-1H-pyrazolo[4,3-c]quinoline (DMSO-d$_6$, δ): 0.97 (3H, t, J=7.6 Hz), 2.46 (2H, q, J=7.6 Hz), 4.85 (2H, s), 7.30 (1H, d,d.; J=1.8, 8.6 Hz), 7.57 (1H, d, J=8.6 Hz), 7.71 (1H, s), 7.74 (1H, d, J=1.8 Hz), 13.05 (1H, br s)

(9) 8-Chloro-4,5-dihydro-1-isopropyl-5-propionyl-1H-pyrazolo[4,3-c]quinoline

NMR (CDCl$_3$, δ): 1.13 (3H, t, J=7 Hz), 1.63 (6H, d, J=7 Hz), 2.51 (2H, q, J=7 Hz), 4.85 (2H, s), 4.95 (1H, sept, J=7 Hz), 7.40 (1H, d, J=2 Hz), 7.43 (1H, s), 7.53 (1H, s), 7.62 (1H, d, J=2 Hz)

(10) 8-Chloro-4,5-dihydro-1-(2-dimethylaminoethyl)-5-propionyl-1H-pyrazolo[4,3-c]quinoline NMR (CDCl$_3$, δ): 1.13 (3H, t, J=7 Hz), 2.35 (6H, s), 2.49 (2H, q, J=7 Hz), 2.90 (2H, t, J=7 Hz), 4.57 (2H, t, J=7 Hz), 4.87 (2H, s), 7.42 (1H, d, J=2 Hz), 7.43 (1H, s), 7.52 (1H, s), 7.87 (1H, d, J=2 Hz) (11) 8-Chloro-4,5-dihydro-5-(2,3-dimethylpentanoyl)-1H-pyrazolo [4,3-c]quinoline NMR (DMSO-d$_6$, δ): 0.63 (3H, t, J=6 Hz), 0.68 (3H, d, J=6 Hz), 1.00 (3H, d, J=6 Hz), Ca. 0.9–1.8 (3H, m), Ca. 2.6–3.1 (1H, m), 4.41 (1H, d, J=14 Hz), 5.35 (1H, d, J=14 Hz), 7.40 (2H, br s), 7.74 (2H, br s), 13.03 (1H, br s)

(12) 8-Chloro-4,5-dihydro-5-ethanesulfonyl-1H-pyrazolo[4,3,-c]quinoline

NMR (DMSO-d$_6$, δ): 0.92 (3H, t, J=8 Hz), 2.80 (2H, q, J=8 Hz), 4.82 (2H, s), 7.34 (1H, d,d, J=2, 9 Hz), 7.58 (1H, d, J=9 Hz), 7.77 (1H, d, J=2 Hz), 13.13 (1H, br s)

(13) 8-Chloro-4,5-dihydro-5-myristoyl-1H-pyrazolo[4,3-c]quinoline

NMR (DMSO-d$_6$, δ): 0.86 (3H, t, J=6 Hz), 0.95–1.64 (22H, m), Ca. 2.3–2.6 (2H), 4.84 (2H, s), 7.32 (1H, d,d, J=2, 8 Hz), 7.53 (1H, d, J=8 Hz), 7.72 (2H, br s), 13.02 (1H, br s)

(14) 8-Chloro-4,5-dihydro-5-methanesulfonyl-1H-pyrazolo [4,3-c]quinoline

NMR (DMSO-d$_6$, δ): 2.61 (3H, s), 4.90 (2H, s), 7.45 (1H, d,d, J=2, 9 Hz), 7.64 (1H, d, J=9 Hz), 7.80 (1H, s), 7.88 (1H, d, J=2 Hz), Ca. 13.0 (1H, br s)

(15) 8-Chloro-4,5-dihydro-5-ethylcarbamoyl-1H-pyrazolo [4,3-c]quinoline

NMR (DMSO-d$_6$, δ): 1.03 (3H, t, J=7 Hz), 2.86-Ca. 3.3, (2H, m), 4.69 (2H, s), 6.74 (1H, b.t., J=5 Hz), 7.23 (1H, d,d, J=2, 8 Hz), 7.43 (1H, d, J=8 Hz), 7.66 (2H, d, J=2 Hz), 13.0 (1H, br)

(16) 8-Chloro-4,5-dihydro-5-ethoxycarbonyl-1H-pyrazolo [4,3-c]quinoline

NMR (DMSO-d$_6$, δ): 1.21 (3H, t, J=7 Hz), 4.16 (2H, q, J=7 Hz), 4.81 (2H, s), 7.30 (1H, d,d, J=2, 8 Hz), 7.61 (1H, d, J=8 Hz), 7.71 (2H, br s), 13.0 (1H, br s)

(17) 8-Chloro-5-cyclopropylcarbonyl-4,5-dihydro-1H-pyrazolo[4,3-c]quinoline

NMR (DMSO-d$_6$, δ): 0.66–1.13 (4H, m), 1.63–2.1 (1H, m), 4.87 (2H, s), 7.35 (1H, d,d, J=2, 8 Hz), 7.58 (1H, d, J=8 Hz), 7.74 (2H, d, J=2 Hz), 12.96 (1H, br s)

(18) 4,5-Dihydro-8-hydroxy-5-propionyl-1H-pyrazolo-[4,3-c]quinoline

NMR (DMSO-d$_6$, δ): 0.93 (3H, t, J=7 Hz), 2.37 (2H, q, J=7 Hz), 4.77 (2H, s), 6.68 (1H, d,d, J=2, 8 Hz), 7.15 (1H, d, J=2 Hz), 7.28 (1H, d, J=8 Hz), 7.63 (1H, br s), 9.56 (1H, br s), 12.83 (1H, br s)

(19) 4,5-Dihydro-8-(N-methyl-N-mesylamino)-5-propionyl-1H-pyrazolo [4,3-c]quinoline NMR (DMSO-d$_6$, δ): 1.01 (3H, t, J=7 Hz), 2.49 (2H, q, J=7 Hz), 3.0 (3H, s), 3.28 (3H, s), 4.83 (2H, s), 7.29 (1H, d,d; J=2, 8 Hz), 7.54 (1H, d, J=8 Hz), 7.66 (1H, s), 7.74 (1H, d, J=2 Hz), 13.0 (1H, br s)

(20) 4,5-Dihydro-8-methoxy-5-propionyl-1H-pyrazolo [4,3-c]quinoline

NMR (DMSO-d$_6$, δ): 0.97 (3H, t, J=7 Hz), 2.39 (2H, q, J=7 Hz), 3.85 (3H, s), 4.83 (2H, s), 6.88 (1H, d,d; J=2, 8 Hz), 7.32 (1H, d, J=2 Hz), 7.42 (1H, d, J=8 Hz), 7.67 (1H, br s), 12.92 (1H, br s)

(21) 8-Acetamido-4,5-dihydro-5-propionyl-1H-pyrazolo[4,3-c]quinoline

NMR (DMSO-d$_6$, δ): 0.97 (3H, t, J=7 Hz), 2.09 (3H, s), 2.42 (2H, q, J=7 Hz), 4.79 (2H, s), 7.39 (2H, s), 7.59 (1H, s), 8.02 (1H, d, J=2 Hz), 9.93 (1H, s), 12.93 (1H, br s)

(22) 8,9-Dichloro-4,5-dihydro-5-propionyl-1H-pyrazolo[4,3-c]quinoline

NMR (DMSO-d$_6$, δ): 0.97 (3H, t, J=7 Hz), 2.43 (2H, q, J=7 Hz), 4.80 (2H, s), 7.53 (2H, s), 7.75 (1H, s), 13.20 (1H, br s)

(23) 6,8-Dichloro-4,5-dihydro-5-propionyl-1H-pyrazolo[4,3-c]quinoline

NMR (DMSO-d$_6$, δ): 0.96 (3H, t, J=7 Hz), 2.40 (2H, br s), 4.04 (1H, br s), 5.60 (1H, br s), 7.59 (1H, d, J=2 Hz), 7.76 (2H, s), 13.15 (1H, s)

(24) 7,8-Dichloro-4,5-dihydro-5-propionyl-1H-pyrazolo[4,3-c]quinoline

NMR (DMSO-d$_6$, δ): 1.02 (3H, t, J=7 Hz), 2.54 (2H, q, J=7 Hz), 4.87 (2H, s), 7.73 (1H, s), 7.90 (2H, s), 13.11 (1H, s)

(25) 9-Chloro-4,5-dihydro-8-methoxycarbonylmethoxy-5-propionyl-1H-pyrazolo[4,3-c]quinoline NMR (DMSO-d$_6$, δ): 0.92 (3H, t, J=7 Hz), 2.37 (2H, q, J=7 Hz), 3.73 (3H, s), 4.76 (2H, s), 4.97 (2H, s), 7.03 (1H, d, J=9 Hz), 7.46 (1H, d, J=9 Hz), 7.70 (1H, s), 13.1 (1H, br s)

(26) 4,5-Dihydro-8-methoxycarbonylmethoxy-5-propionyl-1H-pyrazolo[4,3-c]quinoline NMR (DMSO-d$_6$, δ): 0.97 (3H, t, J=7 Hz), 2.42 (2H, q, J=7 Hz), 3.76 (3H, s), 4.83 (2H, s), 4.90 (2H, s), 6.92 (1H, d,d; J=2, 9 Hz), 7.30 (1H, d, J=2 Hz), 7.49 (1H, d, J=9 Hz), 7.68 (1H, s), Ca. 13.0 (1H, br s)

(27) 4,5-Dihydro-8-methyl-5-propionyl-1H-pyrazolo[4,3-c]quinoline

NMR (DMSO-d$_6$, δ): 0.97 (3H, t, J=7 Hz), 2.37 (3H, s), Ca. 2.2–2.6 (2H, m), 4.84 (2H, s), 7.12 (1H, d,d; J=2, 8 Hz), 7.38 (1H, d, J=8 Hz), 7.60 (2H, br s), 12.90 (1H, br s)

(28) 8-(4-Chlorophenoxy)-4,5-dihydro-5-propionyl-1H-pyrazolo[4,3-c]quinoline

NMR (CDCl$_3$, δ): 1.11 (3H, t, J=7.5 Hz), 2.46 (2H, q, J=7.5 Hz), 4.94 (2H, s), 6.87–7.48 (8H, m), 12.00 (1H, br s)

(29) 8-Chloro-4,5-dihydro-1-ethyl-5-propionyl-1H-pyrazolo[4,3-c]quinoline

NMR (CDCl$_3$, δ): 1.10 (3H, t, J=7.5 Hz), 1.55 (3H, t, J=6 Hz), 2.44 (2H, q, J=7.5 Hz), 4.42 (2H, q, J=6 Hz), 4.77 (2H, s), 7.30 (1H, d, J=2 Hz), 7.32 (1H, s), 7.37 (1H, s), 7.50 (1H, d, J=2 Hz)

(30) 8-Chloro-4,5-dihydro-1-(2-hydroxyethyl)-5-propionyl-1H-pyrazolo[4,3-c]quinoline NMR (CDCl$_3$, δ): 1.10 (3H, t, J=7 Hz), 2.48 (2H, q, J=7 Hz), 3.63 (1H, br s), 4.08–4.33 (2H, m), 4.53 (2H, t, J=5 Hz), 4.80 (2H, s), 7.30 (1H, d, J=1.5 Hz), 7.32 (1H, s), 7.42 (1H, s), 7.72 (1H, d, J=1.5 Hz)

(31) 8-Chloro-4,5-dihydro-2-methyl-5-propionyl-2H-pyrazolo[4,3-c]quinoline

NMR (CDCl$_3$, δ): 1.08 (3H, t, J=7 Hz), 2.43 (2H, q, J=7 Hz), 3.93 (3H, s), 4.87 (2H, s), 7.23 (3H, s)

(32) 8-Chloro-4,5-dihydro-2-ethyl-5-propionyl-2H-pyrazolo[4,3-c]quinoline

NMR (CDCl$_3$, δ): 1.08 (3H, t, J=7 Hz), 1.50 (3H, t, J=7 Hz), 2.42 (2H, q, J=7 Hz), 4.18 (2H, q, J=7 Hz), 4.88 (2H, s), 7.18 (1H, d, J=1.5 Hz), 7.20 (1H, s), 7.25 (1H, s), 7.85 (1H, d, J=1.5 Hz)

(33) 8-Chloro-4,5-dihydro-2-isopropyl-5-propionyl-2H-pyrazolo[4,3-c]quinoline

NMR (CDCl$_3$, δ): 1.17 (3H, t, J=7.5 Hz), 1.55 (6H, d, J=6 Hz), 2.45 (2H, q, J=7.5 Hz), 4.58 (1H, quint, J=6 Hz), 4.93 (2H, s), 7.25 (1H, d, J=1.5 Hz), 7.27 (1H, s), 7.33 (1H, s), 7.93 (1H, d, J=1.5 Hz)

(34) 8-Chloro-4,5-dihydro-2-allyl-5-propionyl-2H-pyrazolo[4,3-c]quinoline

NMR (CDCl$_3$, δ): 1.08 (3H, t, J=7 Hz), 2.48 (2H, q, J=7 Hz), 4.75–5.42 (4H, m), 4.92 (2H, s), 5.82–6.45 (1H, m), 7.25 (1H, d, J=1.5 Hz), 7.27 (1H, s), 7.32 (1H, s), 7.92 (1H, d, J=1.5 Hz)

(35) 8-Chloro-4,5-dihydro-2-propargyl-5-propionyl2H-pyrazolo[4,3-c]quinoline

NMR (CDCl$_3$, δ): 1.08 (3H, t, J=7.5 Hz), 2.37 (2H, q, J=7.5 Hz), 2.53 (1H, d, J=3 Hz), 4.90 (2H, s), 4.97 (1H, d, J=3 Hz), 7.25 (1H, d, J=1.5 Hz), 7.27 (1H, s), 7.48 (1H, s), 7.83 (1H, d, J=1.5 Hz)

(36) 8-Chloro-4,5-dihydro-5-propionyl-2-(2-methoxyethyl)-2H-pyrazolo[4,3-c]quinoline NMR (CDCl$_3$, δ): 1.10 (3H, t, J=8 Hz), 2.40 (2H, q, J=8 Hz), 3.34 (3H, s), 3.78 (2H, t, J=5 Hz), 4.32 (2H, t, J=5 Hz), 4.90 (2H, s), 7.26 (1H, d, J=1.5 Hz), 7.27 (1H, s), 7.38 (1H, s), 7.89 (1H, d, J=1.5 Hz)

(37) 8-Chloro-4,5-dihydro-5-propionyl-2-(2-oxopropyl)-2H-pyrazolo[4,3-c]quinoline NMR (CDCl$_3$, δ): 1.05 (3H, t, J=7 Hz), 2.13 (3H, s), 2.41 (2H, q, J=7 Hz), 4.88 (4H, s), 7.20 (1H, d, J=1.5 Hz), 7.22 (1H, s), 7.25 (1H, s), 7.78 (1H, d, J=1.5 Hz)

(38) 8-Chloro-4,5-dihydro-2-ethoxycarbonylmethyl5-propionyl-2H-pyrazolo[4,3-c]quinoline NMR (CDCl$_3$, δ): 1.10 (3H, t, J=7 Hz), 1.28 (3H, t, J=7 Hz), 2.44 (2H, q, J=7 Hz), 4.20 (2H, q, J=7 Hz), 4.92 (4H, s), 7.22 (1H, d, J=1.5 Hz), 7.23 (1H, s), 7.35 (1H, s), 7.85 (1H, d, J=1.5 Hz)

(39) 8-Chloro-4,5-dihydro-2-[2-(N,N-dimethylaminoethyl]-5-propionyl-2H-pyrazolo[4,3-c]quinoline NMR (CDCl$_3$, δ): 1.10 (3H, t, J=7.5 Hz), 2.32 (6H, s), 2.43 (2H, q, J=7.5 Hz), 2.78 (2H, t, J=7 Hz), 4.23 (2H, t, J=7 Hz), 4.89 (2H, s), 7.21 (1H, d, J=1.5 Hz), 7.23 (1H, s), 7.35 (1H, s), 7.85 (1H, d, J=1.5 Hz)

(40) 8-Chloro-4,5-dihydro-5-propionyl-2-n-tetradecyl-2H-pyrazolo[4,3-c]quinoline NMR (CDCl$_3$, δ): 0.74–2.06 (24H, m), 1.10 (3H, t, J=8 Hz), 2.39 (2H, q, J=8 Hz), 4.15 (2H, t, J=7 Hz), 4.92 (2H, s), 7.26 (1H, d, J=1.5 Hz), 7.27 (2H, s), 7.91 (1H, d, J=1.5 Hz) p (41) 2-Benzyl-8-chloro-4,5-dihydro-5-propionyl-2H-pyrazolo[4,3-c]quinoline NMR (CDCl$_3$, δ): 1.10 (3H, t, J=7.5 Hz), 2.44 (2H, q, J=7.5 Hz), 4.88 (2H, s), 5.33 (2H, s), 7.25 (1H, d, J=1.5 Hz), 7.27 (2H, s), 7.35 (7H, s), 7.93 (1H, d, J=1.5 Hz)

(42) 8-Chloro-4,5-dihydro-1-allyl-5-propionyl-1H-pyrazolo[4,3-c]quinoline

NMR (CDCl$_3$, δ): 1.10 (3H, t, J=7 Hz), 2.45 (2H, q, J=7 Hz), 4.68–5.38 (4H, m), 4.82 (2H, s), 5.77–6.40 (1H, m), 7.32 (1H, d, J=1.5 Hz), 7.33 (1H, s), 7.43 (1H, s), 7.53 (1H, d, J=1.5 Hz)

(43) 8-Chloro-4,5-dihydro-1-ethoxycarbonylmethyl-5-propionyl-1H-pyrazolo[4,3-c]quinoline NMR (CDCl$_3$, δ): 1.13 (3H, t, J=7 Hz), 1.28 (3H, t, J=7 Hz), 2.44 (2H, q, J=7 Hz), 4.33 (2H, q, J=7 Hz), 4.87 (2H, s), 5.18 (2H, s), 7.35 (3H, s), 7.47 (1H, s)

(44) 8-Chloro-4,5-dihydro-5-propionyl-1-(2-oxopropyl)-1H-pyrazolo[4,3-c]quinoline NMR (CDCl$_3$, δ): 1.12 (3H, t, J=7 Hz), 2.46 (2H, q, J=7 Hz), 3.35 (3H, s), 3.92 (2H, t, J=5 Hz), 4.55 (2H, t, J=5 Hz), 4.80 (2H, s), 7.30 (1H, d, J=2 Hz), 7.32 (1H, s), 7.43 (1H, s), 7.93 (1H, d, J=2 Hz)

(45) 8-Chloro-4,5-dihydro-5-propionyl-1-n-tetradecyl-1H-pyrazolo[4,3-c]quinoline NMR (CDCl$_3$, δ): 0.73–2.10 (24H, m), 1.13 (3H, t, J=8 Hz), 2.42 (2H, q, J=8 Hz), 4.40 (2H, t, J=7 Hz), 4.82 (2H, s), 7.32 (1H, d), 7.37 (1H, s), 7.40 (1H, s), 7.55 (1H, d)

(46) 8-Carboxymethoxy-4,5-dihydro-5-propionyl-1H-pyrazolo[4,3-c]quinoline

NMR (DMSO-d$_6$, δ): 0.96 (3H, t, J=7 Hz), 2.42 (2H, q, J=7 Hz), 4.76 (2H, s), 4.81 (2H, s), 6.87 (1H, d,d; J=3, 8 Hz), 7.26 (1H, d, J=3 Hz), 7.45 (1H, d, J=8 Hz), 7.63 (1H, s)

(47) 8-Chloro-4,5-dihydro-2-carboxymethyl-5-propionyl-2H-pyrazolo[4,3-c]quinoline NMR (DMSO-d$_6$, δ): 0.98 (3H, t, J=8 Hz), 2.47 (2H, q, J=8 Hz), 4.86 (2H, s), 5.03 (2H, s), 7.36 (1H, dd, J=3 Hz, 9 Hz), 7.59 (1H, d, J=9 Hz), 7.69 (1H, d, J=3 Hz), 7.74 (1H, s),11.33 (1H, br s)

(48) 8-Chloro-4,5-dihydro-5-(3-methoxypropionyl)-1-methyl-1H-pyrazolo[4,3-c]quinoline NMR (CDCl$_3$, δ): 2.63 (2H, t, J=6 Hz), 3.27 (3H, s), 3.50 (2H, t, J=6 Hz), 4.13 (3H, s), 4.80 (2H, s), 7.27 (1H, d, J=2 Hz), 7.28 (1H, s), 7.37 (1H, s), and 7.50 (1H, d, J=2 Hz)

(49) 8-Chloro-4,5-dihydro-1-propargyl-5-propionyl-1H-pyrazolo[4,3-c]quinoline

NMR (CDCl$_3$, δ): 1.14 (3H, t, J=7 Hz), 2.46 (2H, q, J=7 Hz), 2.59 (1H, d, J=3 Hz), 4.86 (2H, s), 5.18 (2H, d, J=3 Hz), 7.39 (1H, d, J=1.5 Hz), 7.40 (1H, s), 7.47 (1H, s) and 7.87 (1H, d, J=1.5 Hz)

(50) 2-(2-Butynyl)-8-chloro-4,5-dihydro-5-propionyl-2H-pyrazolo[4,3-c]quinoline

NMR (CDCl$_3$, δ): 1.10 (3H, t, J=7 Hz), 1.90 (3H, d, J=2 Hz), 2.44 (2H, q, J=7 Hz), 4.90 (2H, s), 4.92 (2H, q, J=2 Hz), 7.18 (1H, s), 7.20 (1H, d, J=2 Hz), 7.45 (1H, s) and 7.83 (1H, d, J=2 Hz)

(51) 8-Chloro-4,5-dihydro-5-formyl-1-methyl-1H-pyrazolo[4,3-c]quinoline
NMR(CDCl$_3$, δ): 4.20(3H, s), 4.86(2H, s), 7.36(1H, s), 7.03-7.46(2H, m), 7.62(1H, d, J=2 Hz), 8.47(1H, s)

EXAMPLE 19

Methylhydrazine(30.56 g) was added dropwise to a mixture of 6-chloro-3-hydroxymethylene-4-oxo-1-propionyl-1,2,3,4-tetrahydroquinoline (160.3 g) and acetic acid(75.8 ml) in methanol (1.6 liters) with stirring and cooling over a period of 10 minutes. After being stirred for 1 hour at room temperature, the mixture was filtered by sunction and the filtrate was evaporated in vacuo after addition of acetic acid (160 ml) to it. The residue was neutralized with aqueous sodium hydroxide under ice cooling. The resulting precipitate was collected by filtration, washed with water and recrystallized from aqueous methanol and then ethanol to give 8-chloro-4,5-dihydro-1-methyl-5-propionyl-1H-pyrazolo[4,3-c]quinoline (65.84 g). The physical data of the compound was identical to that of the object compound of Example 3.

EXAMPLE 20

Methylhydrazine (52.5 g) was dropwise to a mixture of 6-chloro-1-formyl-3-hydroxymethylene-4-oxo-1,2,3,4-tetrahydroquinoline (276 g) and acetic acid (13 ml) in methanol (2.76 liters) at 10° C. to 12° C. over a period of 10 minutes. After being stirred for 1.5 hours at the same temperature, the resulting precipitate was collected by filtration, washed with methanol and dried to give 8-chloro-4,5-dihydro-5-formyl-1-methyl-1H-pyrazolo 4,3-c]quinoline (174 g).

The filtrate was allowed to stand overnight at room temperature and the resulting precipitate was collected by filtration, washed with methanol and dried to give 8-chloro-4,5-dihydro-5-formyl-1-methyl-1H-pyrazolo[4,3-c]quinoline (22.9 g).

IR(Nujol): 1675(sh), 1665, 1470, 1460(sh) cm$^{-1}$
NMR(CDCl$_3$, δ): 4.20 (3H, s), 4.86 (2H, s), 7.36 (1H, s), 7.03-7.46 (2H, m), 7.62 (1H, d, J=2 Hz), 8.47 (1H, s)

EXAMPLE 21 (Preparation of granules or small granules)

| | |
|---|---|
| 8-Chloro-4,5-dihydro-1-methyl-5-propionyl-1H-pyrazolo[4,3-c]quinoline | 5000 (g) |
| Sucrose | 9250 |
| Hydroxypropylcellulose | 200 |
| Starch | 50 |

The above ingredients are blended and granulated or grained in a conventinal manner into granules or small granules.

We claim:

1. A compound of the formula:

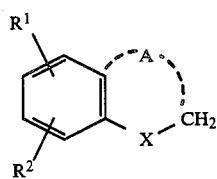

(I)

wherein
R$^1$ is halogen, nitro, amino, hydroxy, lower alkyl, lower alkoxy substituted by carboxy or protected carboxy, acylamino which may have lower alkyl on the amino moiety, or aryloxy which may have halogen,
R$^2$ is hydrogen or halogen,
X is

in which R$^3$ is hydrogen, lower alkyl or acyl and
A is a group of the formula:

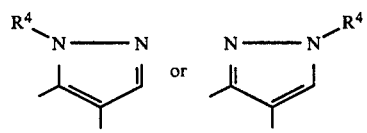

in which
R$^4$ is hydrogen, lower alkenyl, lower alkynyl or alkyl which may have one or more substituents selected from the group consisting of hydroxy, acyl, lower alkoxy, di(lower)alkylamino, carboxy, protected carboxy and aryl; or
R$^1$ is hydrogen of lower alkoxy,
R$^2$ is hydrogen,
X is

in which R$_a^3$ is lower alkanoyl and
A is a group of the formula:

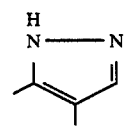

and pharmaceutically acceptable salts thereof, wherein acyl is selected from the group consisting of alkanoyl which may have lower alkoxy, lower cycloalkylcarbonyl, lower alkoxycarbonyl, lower alkanesulfonyl and lower alkylcarbamoyl, and wherein aryl and aryl of aryloxy is selected from the group consisting of phenyl, tolyl, xylyl and naphthyl.

2. A compound of claim 1, in which
R$^1$ is halogen, nitro, amino, hydroxy, lower alkyl, lower alkoxy substituted by carboxy or protected carboxy, acylamino which may have lower alkyl on the amino moiety, or aryloxy which may have halogen,
R$^2$ is hydrogen or halogen,
X is

in which R$^3$ is hydrogen, lower alkyl or acyl and
A is a group of the formula:

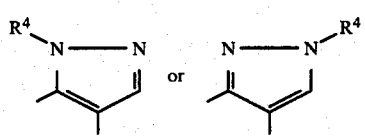 or in which
R⁴ is hydrogen, lower alkenyl, lower alkynyl or alkyl which may have one or more substituents selected from the group consisting of hydroxy, acyl, lower alkoxy, di(lower)alkylamino, carboxy, protected carboxy and aryl.

3. A compound of claim 2, which is a compound of the formula:

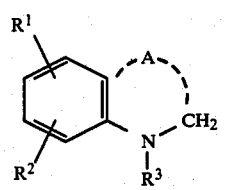

wherein R¹, R², R³ and A are each as defined in claim 2.

4. A compound of claim 3, in which
R² and R³ are each as defined in claim 3,
R¹ is halogen, nitro, amino, hydroxy, lower alkyl, carboxy(lower)alkoxy, esterified carboxy(lower)alkoxy, acylamino, N-lower alkyl-N-acylamino or haloaryloxy and
R⁴ is hydrogen, lower alkenyl, lower alkynyl, lower alkyl, higher alkyl, hydroxy(lower)alkyl, acyl(lower)alkyl, lower alkoxy(lower)alkyl, di(lower)alkylamino(lower)alkyl, carboxy(lower)alkyl, esterified carboxy(lower)alkyl or ar(lower)alkyl.

5. A compound of claim 4, in which
R² is the same as defined in claim 4,
R¹ is halogen, nitro, amino, hydroxy, lower alkyl, carboxy(lower)alkoxy, lower alkoxycarbonyl(lower)alkoxy, lower alkanoylamino, N-lower alkyl-N-lower alkanesulfonylamino or halophenoxy,
R³ is hydrogen, lower alkyl, higher alkanoyl, lower cycloalkylcarbonyl, lower alkoxycarbonyl, lower alkanesulfonyl, lower alkylcarbamoyl or lower alkanoyl which may have lower alkoxy, and
R⁴ is hydrogen, lower alkenyl, lower alkynyl, lower alkyl, higher alkyl, hydroxy(lower)alkyl, lower alkanoyl(lower)alkyl, lower alkoxy(lower)alkyl, di(lower)alkylamino(lower)alkyl, carboxy(lower)alkyl, lower alkoxycarbonyl(lower)alkyl or phenyl(lower)alkyl.

6. A compound of claim 5, in which
R¹ is chlorine, nitro, amino, hydroxy, methyl, carboxymethoxy, methoxycarbonylmethoxy, acetamido, N-methyl-N-mesylamino or chlorophenoxy,
R² is hydrogen or chlorine,
R³ is hydrogen, methyl, 2, 3-dimethylpentanoyl, myristoyl, cyclopropylcarbonyl, ethoxycarbonyl, mesyl, ethanesulfonyl, ethylcarbamoyl, formyl, propionyl or methoxypropionyl, and
R⁴ is hydrogen, allyl, propargyl, butynyl, methyl, ethyl, isopropyl, tetradecyl, hydroxyethyl, 2-oxopropyl, methoxyethyl, dimethylaminoethyl, carboxymethyl, ethoxycarbonylmethyl or benzyl.

7. A compound of claim 5, which is a compound of the formula:

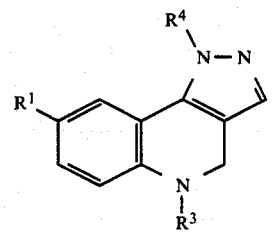

wherein
R¹ is halogen,
R³ is hydrogen or lower alkanoyl and
R⁴ is hydrogen or lower alkyl, or pharmaceutically acceptable salt thereof.

8. A compound of claim 7, which is 8-Chloro-4,5-dihydro-1-methyl-5-propionyl-1H-pyrazolo[4,3-c]quinoline or pharmaceutically acceptable salt thereof.

9. A compound of claim 7, which is 8-Chloro-4,5-dihydro-5-propionyl-1H-pyrazolo[4,3-c]quinoline or pharmaceutically acceptable salt thereof.

10. A compound of claim 7, which is 8-Chloro-4,5-dihydro-1-methyl-1H-pyrazolo[4,3-c]quinoline or pharmaceutically acceptable salt thereof.

11. A compound of claim 7, which is 8-Chloro-4,5-dihydro-1-isopropyl-5-propionyl-1H-pyrazolo-[4,3-c]quinoline or pharmaceutically acceptable salt thereof.

12. A compound of claim 1, in which

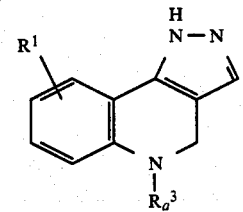

wherein
R¹ is hydrogen or lower alkoxy and
R_a³ is lower alkanoyl.

13. A compound of claim 12, in which
R¹ is hydrogen or methoxy and
R_a³ is propionyl.

14. A diuretic pharmaceutical composition comprising a diuretically effective amount of the compound of claim 1 or pharmaceutically acceptable salt thereof in admixture with a pharmaceutically acceptable carrier.

15. A uricosuric pharmaceutical composition comprising a uricosurically effective amount of the compound of claim 1 or pharmaceutically acceptable salt thereof in admixture with a pharmaceutically acceptable carrier.

16. An antihypertensive pharmaceutical composition comprising an antihypertensively effective amount of the compound of claim 1 or pharmaceutically acceptable salt thereof in admixture with a pharmaceutically acceptable carrier.

17. A method of administering a diuretic agent to a subject in need of such administration which comprises administering a diuretically effective amount of the compound of claim 1 or pharmaceutically acceptable salt thereof.

18. A method of administering a uricosuric agent to a subject in need of such administration which comprises administering a uricosurically effective amount of the compound of claim 1 or pharmaceutically acceptable salt thereof.

19. A method of administering an antihypertensive agent to a subject in need of such administration which comprises administering an antihypertensively effective amount of the compound of claim 1 or pharmaceutically acceptable salt thereof.

* * * * *